US010934573B2

(12) United States Patent
Reid et al.

(10) Patent No.: US 10,934,573 B2
(45) Date of Patent: Mar. 2, 2021

(54) DIAGNOSIS OF BACTERIAL VAGINOSIS

(71) Applicant: LONDON HEALTH SCIENCES CENTRE RESEARCH INC., London (CA)

(72) Inventors: Gregor Reid, Komoka (CA); Amy McMillan, London (CA); Mark Sumarah, London (CA); Jeremy Burton, London (CA); Stephen Rulisa, Kigali (RW)

(73) Assignee: LONDON HEALTH SCIENCES CENTRE RESEARCH INC., London (CA)

(*) Notice: Subject to any disclaimer, the term of this patent is extended or adjusted under 35 U.S.C. 154(b) by 114 days.

(21) Appl. No.: 15/565,633

(22) PCT Filed: Apr. 11, 2016

(86) PCT No.: PCT/CA2016/050415
§ 371 (c)(1),
(2) Date: Oct. 10, 2017

(87) PCT Pub. No.: WO2016/161525
PCT Pub. Date: Oct. 13, 2016

(65) Prior Publication Data
US 2018/0080057 A1   Mar. 22, 2018

Related U.S. Application Data

(60) Provisional application No. 62/146,094, filed on Apr. 10, 2015.

(51) Int. Cl.
*C12Q 1/04* (2006.01)
*C12P 7/42* (2006.01)
*G01N 33/569* (2006.01)

(52) U.S. Cl.
CPC ............. *C12Q 1/04* (2013.01); *C12P 7/42* (2013.01); *G01N 33/56911* (2013.01); *G01N 2333/195* (2013.01); *G01N 2800/52* (2013.01); *G01N 2800/7066* (2013.01)

(58) Field of Classification Search
None
See application file for complete search history.

(56) References Cited

PUBLICATIONS

Amsel, R, et al (1983) Nonspecific vaginitis. diagnostic criteria and microbial and epidemiologic associations. Am J Med 74(1): 14-22.
Chaijareenont K, Sirimai K, Boriboonhirunsarn D & Kiriwat O (2004) Accuracy of Nugent's score and each Amsel's criteria in the diagnosis of bacterial vaginosis. J Med Assoc Thai 87(11): 1270-1274.
Sha, BE, et al (2005) Utility of amsel criteria, nugent score, and quantitative PCR for Gardnerella vaginalis, Mycoplasma hominis, and *Lactobacillus* spp. for diagnosis of bacterial vaginosis in human immunodeficiency virus-infected women. J Clin Microbiol 43(9): 4607-4612.
Schwebke JR, Hillier SL, Sobel JD, McGregor JA & Sweet RL (1996) Validity of the vaginal gram stain for the diagnosis of bacterial vaginosis. Obstet Gynecol 88(4 Pt 1): 573-576.
Mayers JR, et al (2014) Elevation of circulating branched-chain amino acids is an early event in human pancreatic adenocarcinoma development. Nat Med 20(10): 1193-1198.
Sreekumar A, et al (2009) Metabolomic profiles delineate potential role for sarcosine in prostate cancer progression. Nature 457(7231): 910-914.
Theriot CM, et al (2014) Antibiotic-induced shifts in the mouse gut microbiome and metabolome increase susceptibility to Clostridium difficile infection. Nat Commun 5: 3114.
International Search Report and Written Opinion of the International Searching Authority of PCT/CA2016/050415.
Zhou X, et al (2010) The vaginal bacterial communities of Japanese women resemble those of women in other racial groups. FEMS Immunol Med Microbiol 58(2): 169-181.
Ison CA, Easmon CS, Dawson SG, Southerton G & Harris JW (1983) Non-volatile fatty acids in the diagnosis of non-specific vaginitis. J Clin Pathol 36(12): 1367-1370.
Piot P, Van Dyck E, Godts P & Vanderheyden J (1982) The vaginal microbial flora in non-specific vaginitis. Eur J Clin Microbiol 1(5): 301-306.
Ravel, J., et al (2011) Vaginal microbiome of reproductive-age women. Proc Natl Acad Sci U S A 108 Suppl 1: 4680-4687.
Hummelen, R, et al (2010) Deep sequencing of the vaginal microbiota of women with HIV. PLoS One 5(8): e12078.
Fredricks, DN, Fiedler TL & Marrazzo JM (2005) Molecular identification of bacteria associated with bacterial vaginosis. N Engl J Med 353(18): 1899-1911.
Koumans EH, et al (2007) The prevalence of bacterial vaginosis in the united states, 2001-2004; associations with symptoms, sexual behaviors, and reproductive health. Sex Transm Dis 34(11): 864-869.
Klebanoff, MA, et al (2004) Vulvovaginal symptoms in women with bacterial vaginosis. Obstet Gynecol104(2): 267-272.
Sobel, JD, Karpas, Z & Lorber, A (2012) Diagnosing vaginal infections through measurement of biogenic amines by ion mobility spectrometry. Eur J Obstet Gynecol Reprod Biol. 163(1):81-4.
Wolrath, H, Forsum, U, Larsson, PG & Boren, (2001) Analysis of bacterial vaginosis-related amines in vaginal fluid by gas chromatography and mass spectrometry. J Clin Microbiol39(11): 4026-4031.
Wolrath, H, Stahlbom, B, Hallen, A & Forsum, U (2005) Trimethylamine and trimethylamine oxide levels in normal women and women with bacterial vaginosis reflect a local metabolism in vaginal secretion as compared to urine. Apmis113(7-8): 513-516.
Sha, BE, et al (2005) Female genital-tract HIV load correlates inversely with *Lactobacillus* species but positively with bacterial vaginosis and mycoplasma hominis. J Infect Dis 191(1): 25-32.
Das, TR, Jahan, S, Begum, SR & Akhtar, MF (2011) Association between bacterial vaginosis and preterm delivery. Mymensingh Med J 20(1): 115-120.

(Continued)

*Primary Examiner* — Vera Afremova
(74) *Attorney, Agent, or Firm* — Eduardo Krupnik

(57) ABSTRACT

A method of diagnosing bacterial vaginosis (BV) in a female subject including: (a) obtaining an appropriate sample from the subject; and (b) detecting the presence of at least one of 2-hydroxyisovalerate (2HV) and γ-hydroxybutyrate (GHB) in the sample.

14 Claims, 13 Drawing Sheets

(56) References Cited

PUBLICATIONS

Nugent, RP, Krohn, MA & Hillier, SL (1991) Reliability of diagnosing bacterial vaginosis is improved by a standardized method of gram stain interpretation. J Clin Microbiol 29(2): 297-301.

Al-Mushrif S, Eley A & Jones BM (2000) Inhibition of chemotaxis by organic acids from anaerobes may prevent a purulent response in bacterial vaginosis. J Med Microbiol 49(11): 1023-1030.

Kaneuchi C, Seki M & Komagata K (1988) Production of succinic acid from citric acid and related acids by Lactobacillus strains. Appl Environ Microbiol 54(12): 3053-3056.

Sohling B & Gottschalk G (1996) Molecular analysis of the anaerobic succinate degradation pathway in Clostridium kluyveri. J Bacteriol 178(3): 871-880.

Scherf U, Sohling B, Gottschalk G, Linder D & Buckel W (1994) Succinate-ethanol fermentation in Clostridium kluyveri: Purification and characterisation of 4-hydroxybutyryl-CoA dehydratase/vinylacetyl-CoA delta 3-delta 2-isomerase. Arch Microbiol 161(3): 239-245.

Macklaim JM, et al (2013) Comparative meta-RNA-seq of the vaginal microbiota and differential expression by Lactobacillus iners in health and dysbiosis. Microbiome 1(1): 12-2618-1-12.

Liebich HM & Forst C (1984) Hydroxycarboxylic and oxocarboxylic acids in urine: Products from branched-chain amino acid degradation and from ketogenesis. J Chromatogr 309(2): 225-242.

Kawai S, et al (1996) Purification and characterization of a malic enzyme from the ruminal bacterium *Streptococcus bovis* ATCC 15352 and cloning and sequencing of its gene. Appl Environ Microbiol 62(8): 2692-2700.

Pine L, Malcolm GB, Brooks JB & Daneshvar MI (1989) Physiological studies on the growth and utilization of sugars by *Listeria* species. Can J Microbiol 35(2): 245-254.

Novak L & Loubiere P (2000) The metabolic network of Lactococcus lactis: Distribution of (14)C-labeled substrates between catabolic and anabolic pathways. J Bacteriol 182(4): 1136-1143.

Yeoman CJ, et al (2013) A multi-omic systems-based approach reveals metabolic markers of bacterial vaginosis and insightinto the disease. PLoS One 8(2): e56111.

Kohlmeier KA, Vardar B & Christensen MH (2013) Gamma-hydroxybutyric acid induces actions via the GABAB receptor in arousal and motor control-related nuclei: Implications for therapeutic actions in behavioral state disorders. Neuroscience 248: 261-277.

Absalom N, et al (2012) alpha4betadelta GABA(A) receptors are high-affinity targets for gamma-hydroxybutyric acid (GHB). Proc Natl Acad Sci U S A 109(33): 13404-13409.

Connelly WM, Errington AC & Crunelli V (2013) Gamma-hydroxybutyric acid (GHB) is not an agonist of extrasynaptic GABAA receptors. PLoS One 8(11): e79062.

Laghi L, et al (2014) Rifaximin modulates the vaginal microbiome and metabolome in women affected by bacterial vaginosis. Antimicrob Agents Chemother 58(6): 3411-3420.

Gajer P, et al (2012) Temporal dynamics of the human vaginal microbiota. Sci Transl Med 4(132): 132ra52.

Gloor GB, et al (2010) Microbiome profiling by Illumina sequencing of combinatorial sequence-tagged PCR products. PLoS One 5(10): e15406.

Benjamini, Y. & Hochberg, Y. Controlling the false discovery rate: A practical and powerful approach to multiple testing. J. R. Statist. Soc. B. 57, 289-300 (1995).

Fernandes AD, et al (2014) Unifying the analysis of high-throughput sequencing datasets: Characterizing RNA-seq, 16S rRNA gene sequencing and selective growth experiments by compositional data analysis. Microbiome 2: 15-2618-2-15.

Stein S. (1999) An integrated method for spectrum extraction and compound identification from GC/MS data. J Am Soc Mass Spectrom10: 70-781.

Styczynski MP, et al (2007) Systematic identification of conserved metabolites in GC/MS data for metabolomics and biomarker discovery. Anal Chem79(3): 966-973.

Kessner D, Chambers M, Burke R, Agus D & Mallick P (2008) ProteoWizard: Open source software for rapid proteomics tools development. Bioinformatics 24(21): 2534-2536.

Pluskal T, Castillo S, Villar-Briones A & Oresic M M (2010) MZmine 2: Modular framework for processing, visualizing, and analyzing mass spectrometry-based molecular profile data. BMC Bioinformatics 11: 395-2105-11-395.

Smith CA, et al (2005) METLIN: A metabolite mass spectral database. Ther Drug Monit 27(6): 747-751.

Wishart DS, et al (2013) HMDB 3.0—the human metabolome database in 2013. Nucleic Acids Res 41(Database issue): D801-7.

Lopez-Raton, M. et al. (2014) Optimal Cutpoints: An R Package for Selecting Optimal Cutpoints in Diagnostic Tests. J Stat Softw. 61: 1-36.

Youden WJ (1950) Index for rating diagnostic tests. Cancer 3(1): 32-35.

Friedman, J. & Alm, E. J. Inferring correlation networks from genomic survey data. PLoS Comput. Biol. 8, e1002687 (2012).

Fernandes, A. D., Macklaim, J. M., Linn, T. G., Reid, G. & Gloor, G. B. ANOVA-like differential expression (ALDEx) analysis for mixed population RNA-Seq. PLoS One 8, e67019 (2013).

C

| Ratio | AUC |
|---|---|
| 2-HV:tyrosine | 0.993 |
| 2-HV:lactate | 0.992 |
| GHB:tyrosine | 0.980 |
| GHB:lactate | 0.955 |
| succinate:lactate | 0.756 |

D

| Metabolite | AUC |
|---|---|
| High 2-HV | 0.989 |
| Low tyrosine | 0.965 |
| High GHB | 0.938 |
| Low lactate | 0.930 |
| High succinate | 0.708 |

FIG. 3 (Continued)

DIAGNOSIS OF BACTERIAL VAGINOSIS

FIELD OF THE INVENTION

The field of this invention relates to markers of bacterial vaginosis and to diagnosis of bacterial vaginosis.

BACKGROUND OF THE INVENTION

The vaginal microbiota is dominated by *Lactobacillus* species in most women, predominately by *L. iners* and *L. crispatus* (1-3). When these *lactobacilli* are displaced by a group of mixed anaerobes, belonging to the genus *Gardnerella, Prevotella, Atopobium* and others, this increase in bacterial diversity can lead to bacterial vaginosis (BV) (1-3). BV is the most common vaginal condition, affecting an estimated 30% of women at any given time (4). While many women remain asymptomatic (2-5), when signs and symptoms do arise they include an elevated vaginal pH>4.5, discharge, and malodour due to amines (6-8). BV is also associated with a number of co-morbidities, including increased transmission and acquisition of HIV and other sexually transmitted infections (9), and increased risk of preterm labour (10).

In most instances, diagnosis is dependant upon microscopy of vaginal fluid to identify BV-like bacteria alone (Nugent Scoring (11)), or in combination with clinical signs (Amsel Criteria (12)). The precision and accuracy of these methods are poor due to the diverse morphology of vaginal bacteria, the observation that many women with BV are asymptomatic, and subjectivity in microscopic examination (13-15). Misdiagnosis creates stress for the patient, delays appropriate intervention and places a financial burden on the health care system. A rapid test based on stable, specific biomarkers for BV would improve diagnostic accuracy and speed, and reduce costs through improved patient management.

Metabolomics, defined as the complete set of small molecules in a given environment, has been utilized in a variety of systems to identify biomarkers of disease (16,17), and provide functional insight into shifts in microbial communities (18).

A rapid test based on a well characterized consistent marker for bacterial vaginosis would improve diagnostic accuracy of BV and decrease time required for diagnosis and treatment, potentially preventing preterm labour and other complications including acquisition of sexually transmitted infections.

SUMMARY OF THE INVENTION

The present invention relates to novel markers of bacterial vaginosis and to diagnosis of bacterial vaginosis.

In one embodiment, the present invention is a method for detecting the presence of bacterial vaginosis (BV) in a female subject. The method, in one embodiment, includes: (a) obtaining a sample from the vaginal region of the subject; (b) detecting at least one of 2-hydroxyisovalerate and γ-hydroxybutyrate (GHB) present in the sample, wherein the detection of at least one of 2-hydroxyisovalerate and γ-hydroxybutyrate (GHB) indicates the presence of bacterial vaginosis in the subject.

In one embodiment of the method of the present invention, the method further comprises the step of correlating the presence of detected 2-hydroxyisovalerate and/or γ-hydroxybutyrate (GHB) with the presence of bacterial diversity.

The present invention relates to the use metabolomic profiling or individual metabolites as biomarkers to diagnose BV.

In one embodiment, the present invention is a method of diagnosing bacterial vaginosis (BV) in a female subject comprising: (a) obtaining an appropriate sample from the subject; and (b) detecting the presence of at least one of 2-hydroxyisovalerate (2HV) and γ-hydroxybutyrate (GHB) in the sample, wherein the presence of at least one of 2HV and GHB indicates BV diagnosis in the subject.

In one embodiment of the method of diagnosing BV of the present invention, the ratio of at least one of 2HV and GHB to another metabolite in the sample is calculated, and wherein said diagnosis is based on the ratio.

In another embodiment of the method of diagnosing BV of the present invention, the presence of at least one of 2HV and GHB is detected using high performance liquid chromatography, thin layer chromatography (TLC), electrochemical analysis, Mass Spectroscopy (MS), refractive index spectroscopy (RI), Ultra-Violet spectroscopy (UV), fluorescent analysis, radiochemical analysis, Near-InfraRed spectroscopy (Near-IR), Nuclear Magnetic Resonance spectroscopy (NMR), fluorescence spectroscopy, dual polarisation interferometry, computational methods, Light Scattering analysis (LS), gas chromatography (GC), or GC coupled with MS (GC-MS), direct injection (DI) coupled with LC-MS/MS.

In another embodiment of the method of diagnosing BV of the present invention, the presence of 2HV or GHB is detected using GC-MS, the ratio of at least one of 2HV and GHB to tyrosine in the sample is calculated, and wherein said diagnosis is based on the ratio.

In another embodiment of the method of diagnosing BV of the present invention, the ratio of GHB to tyrosine is 0.6 or above for BV diagnosis.

In another embodiment of the method of diagnosing BV of the present invention, the ratio of 2-HV to tyrosine is 0.8 or above for BV diagnosis.

In another embodiment of the method of diagnosing BV of the present invention, the method does not rely on detecting or measuring the presence of succinate in the sample.

In another embodiment, the present invention is a method of diagnosing bacterial vaginosis (BV) in a female subject including: (a) obtaining an appropriate sample from the subject; and (b) obtaining a level of at least one metabolite in the sample and comparing the level of the at least one metabolite in the sample to the level of said at least one metabolite in a known normal sample (control sample), wherein the presence of the at least one metabolite in relatively higher levels than in the normal sample indicates BV diagnosis in the subject, and wherein the metabolite is selected from the group consisting of 2-hydroxyisovalerate (2HV), γ-hydroxybutyrate (GHB), methyl phosphate, 2-hydroxyglutarate, 5-aminovalerate, 2-hydroxyisocaproate, 2-hydroxy-3-methylvalerate, mannose-6-phosphate, 2-O-glycerol-d-galactopyranoside, beta-alanine, phenylethylamine and n-acetyl-putrescine.

In one embodiment of the previous method, a ratio of the level of the at least one metabolite to the level of another metabolite in the sample is calculated, and the diagnosis is based on the ratio.

In another embodiment of the method of diagnosing BV, the level of the at least one metabolite is detected using high performance liquid chromatography, thin layer chromatography (TLC), electrochemical analysis, Mass Spectroscopy (MS), refractive index spectroscopy (RI), Ultra-Violet spectroscopy (UV), fluorescent analysis, radiochemical analysis, Near-InfraRed spectroscopy (Near-IR), Nuclear Magnetic Resonance spectroscopy (NMR), fluorescence spectroscopy, dual polarisation interferometry, computational methods, Light Scattering analysis (LS), gas chromatography (GC), or GC coupled with MS (GC-MS), direct injection (DI) coupled with LC-MS/MS.

In another embodiment of the method of diagnosing BV, the method does not rely on obtaining the level of succinate in the sample.

In one embodiment of the method of any of the previous embodiments, the sample is a sample of vaginal fluid.

In one embodiment of the method according to any of the previous embodiments, the method further includes specific pathogenic bacterial quantification. In one aspect, the specific pathogenic bacteria is selected from the group consisting of *G. vaginalis* and bacteria of the genera *Dialister*, *Prevotella* and *Atopobium*.

The present invention, in another embodiment, provides for a method of treating bacterial vaginosis (BV) in a patient, the method including obtaining a metabolic profile of the patient, correlating each metabolite of the metabolic profile with a bacterium, and administering the patient a drug or drugs that are effective against the correlated bacterium.

In one embodiment of the method of treating BV of the present invention, the metabolic profile includes γ-hydroxybutyrate (GHB), and wherein drug or drugs are effective against *G. vaginalis*.

In another embodiment of the method of treating BV of the present invention, the metabolic profile includes 2-hydroxyisovalerate (2HV), and wherein the drug or drugs are effective against bacteria of the genera *Dialister*, *Prevotella* and *Atopobium*.

The present invention, in another embodiment, provides for a method of determining the efficacy of a bacterial vaginosis (BV) treatment in a patient undergoing BV treatment, the method including: (a) obtaining an appropriate sample of the patient at different stages of the treatment; (b) obtaining the levels of at least one of 2-hydroxyisovalerate (2HV) and γ-hydroxybutyrate (GHB) in the samples, wherein a progressive decrease in the levels of 2HV and GHB along the stages is indicative of the efficacy of the treatment.

In one embodiment of the method of determining the efficacy of BV treatment of the present invention, the levels of at least one of 2HV and GHB is detected using high performance liquid chromatography, thin layer chromatography (TLC), electrochemical analysis, Mass Spectroscopy (MS), refractive index spectroscopy (RI), Ultra-Violet spectroscopy (UV), fluorescent analysis, radiochemical analysis, Near-InfraRed spectroscopy (Near-IR), Nuclear Magnetic Resonance spectroscopy (NMR), fluorescence spectroscopy, dual polarisation interferometry, computational methods, Light Scattering analysis (LS), gas chromatography (GC), or GC coupled with MS (GC-MS), direct injection (DI) coupled with LC-MS/MS.

In one embodiment of the method of determining the efficacy of BV treatment of the present invention, the ratio of the levels of at least one of 2HV and GHB to the level of another metabolite in the sample is calculated, and wherein said efficacy is determined on a decrease or an increase in the ratio.

In one embodiment of the method of determining the efficacy of BV treatment of the present invention, the levels of at least one of 2HV and GHB is detected using GC-MS, the other metabolite is tyrosine, and wherein said efficacy is based on the ratio of at least one of 2HV and GHB to tyrosine.

The present invention, in another embodiment, provides for a method of determining the efficacy of a bacterial vaginosis (BV) treatment in a patient undergoing BV treatment, the method comprising obtaining an appropriate sample of the patient at different stages of the treatment; (b) obtaining the levels of at least one metabolite selected from the group consisting of 2-hydroxyisovalerate (2HV), γ-hydroxybutyrate (GHB), methyl phosphate, 2-hydroxyglutarate, 5-aminovalerate, 2-hydroxyisocaproate, 2-hydroxy-3-methylvalerate, mannose-6-phosphate, 2-O-glycerol-d-galactopyranoside, beta-alanine, phenylethylamine and n-acetyl-putrescine in the samples, wherein a progressive decrease in the levels of the at least one metabolite along the different stages is indicative of the efficacy of the treatment.

In one embodiment of the previous embodiment, the levels are obtained as a ratio of the at least one metabolite to the level of another metabolite. In one aspect of this embodiment the other metabolite is tyrosine.

The present invention, in another embodiment, provides for a method of diagnosing bacterial vaginosis (BV) in a subject including: (a) obtaining a metabolite profile from the subject; and (b) using multivariate statistical analysis and machine learning to compare the subject's profile with a predetermined set of metabolite profiles of BV and a predetermined set of metabolite profiles of non-BV (referred to as "control" or "normal") to determine if the subject has BV.

In one embodiment of the previous diagnostic method, the subject's metabolite profile and the predetermined set of metabolite profiles are obtained using metabolomics.

In another embodiment of the previous diagnostic method, the metabolomics is performed with one or more of high performance liquid chromatography, thin layer chromatography, electrochemical analysis, mass spectroscopy (MS), refractive index spectroscopy, ultra-violet spectroscopy, fluorescent analysis, radiochemical analysis, near-infrared spectroscopy, nuclear magnetic resonance (NMR), light scattering analysis, gas chromatography (GC), or GC coupled with MS, direct injection (DI) coupled with LC-MS/MS.

In another embodiment of the previous diagnostic method, the steps of the method are executed using a suitably programmed computer.

In another embodiment of the previous diagnostic method, metabolite profiles are obtained from a biological sample.

In another embodiment of the previous diagnostic method, wherein the metabolite includes at least one of 2-hydroxyisovalerate (2HV) and γ-hydroxybutyrate (GHB).

In another embodiment of the previous diagnostic method, the metabolite include 2-hydroxyisovalerate (2HV), γ-hydroxybutyrate (GHB), methyl phosphate, 2-hydroxyglutarate, 5-aminovalerate, 2-hydroxyisocaproate, 2-hydroxy-3-methylvalerate, mannose-6-phosphate, 2-O-glycerol-d-galactopyranoside, beta-alanine, phenylethylamine and n-acetyl-putrescine.

The present invention, in another embodiment, is a use of a metabolic profile of an appropriate sample obtained from a bacterial vaginosis (BV) patient to correlate the metabolic profile of the patient with specific bacteria, and to select a drug to treat the patient based on said specific bacteria.

In one embodiment according to any of the previous embodiments, the appropriate sample is a sample obtained from the vaginal region, including vaginal fluids.

The present invention, in another embodiment, relates to the use of *G. vaginails* for the production of GHB.

BRIEF DESCRIPTION OF THE DRAWINGS

The following figures illustrate various aspects and preferred and alternative embodiments of the invention.

DESCRIPTION OF THE INVENTION

Definitions

Figure 1:
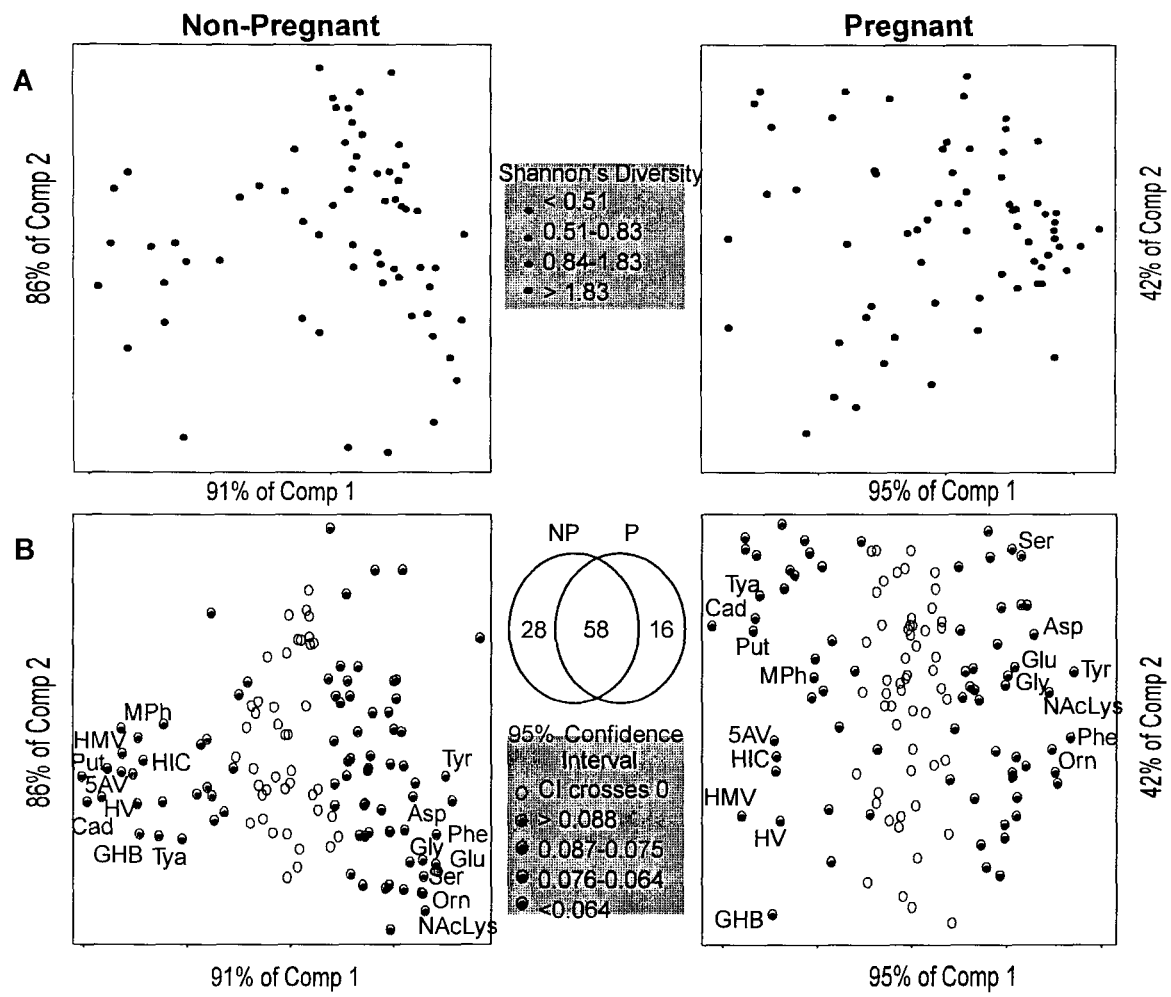
FIG. 1: The vaginal metabolome is most correlated with bacterial diversity. All analyses were carried out independently for non-pregnant (left) and pregnant (right) cohorts. Row (A) Partial least squares regression (PLS) score plot built from 128 metabolites detected by GC-MS using bacterial diversity as a continuous latent variable. Each point represents a single woman (n=131). The position of points displays similarities in the metabolome, with samples closest to one another being most similar. Circles are colored by diversity of the microbiota measured using Shannon's diversity, where darker circles indicate higher diversity. Row (B) PLS regression loadings. Each point represents a single metabolite. Shaded circles indicate metabolites robustly associated with diversity in either cohort (Jackknifing, 95% CI). Shading of circles corresponds to the size of the confidence interval (CI) for each metabolite, where darker circles indicate narrower CIs. Venn diagram depicts overlap between metabolites associated with diversity in either cohort. Cad: Cadaverine, Tya: Tyramine, Put: Putrescine, MPh: Methylphosphate, 5AV: 5-aminovalerate, HIC: 2-hydroxyisocaproate, HMV: 2-hydroxy-3-methylvalerate, HV: 2-hydroxyisovalerate, GHB: γ-hydroxybutyrate. Ser: serine, Asp: aspartate, Glu: glutamate, Gly: glycine, Tyr: tyrosine. NAcLys: n-acetyl-lysine, Phe: phenylalanine, Orn: ornithine.

Unless defined otherwise, all technical and scientific terms used herein have the same meaning as commonly understood by one of ordinary skill in the art to which this invention belongs. Also, unless indicated otherwise, except within the claims, the use of "or" includes "and" and vice versa. Non-limiting terms are not to be construed as limiting unless expressly stated or the context clearly indicates otherwise (for example "including", "having" and "comprising" typically indicate "including without limitation"). Singular forms including in the claims such as "a", "an" and "the" include the plural reference unless expressly stated otherwise. In order to aid in the understanding and preparation of the within invention, the following illustrative, non-limiting, examples are provided.

"Vaginal bacteria" refers to bacteria, alive or dead, that is found in the female vagina and associated tissues and fluids.

"Metabolome" refers to the collection of all metabolites in a biological cell, tissue, organ or organism, which are the end products of cellular processes. "Metabolome" includes lipidome, sugars, nucleotides and amino acids. Lipidome is the complete lipid profile in a biological cell, tissue, organ or organism.

"Metabolomic profiling" refers to the characterization and/or measurement of the small molecule metabolites in biological specimen or sample, including cells, tissue, organs, organisms, swabs, including vaginal swabs, samples of the vaginal region, or any derivative fraction thereof and fluids such as blood, blood plasma, blood serum, saliva, synovial fluid, spinal fluids, urine, bronchoalveolar lavage, tissue extracts, sweat, vaginal fluids and so forth.

The metabolite profile may include information such as the quantity and/or type of small molecules present in the sample. The ordinarily skilled artisan would know that the information which is necessary and/or sufficient will vary depending on the intended use of the "metabolite profile."

For example, the "metabolite profile," can be determined using a single technique for an intended use but may require the use of several different techniques for another intended use depending on such factors as the disease state involved, the types of small molecules present in a particular targeted cellular compartment, the cellular compartment being assayed per se., and so forth.

The relevant information in a "metabolite profile" may also vary depending on the intended use of the compiled information, e.g. spectrum. For example, for some intended uses, the amounts of a particular metabolite or a particular class of metabolite may be relevant, but for other uses the distribution of types of metabolites may be relevant.

Metabolite profiles may be generated by several methods, e.g., high liquid chromatography (HPLC), thin layer chromatography (TLC), electrochemical analysis, Mass Spectroscopy (MS), refractive index spectroscopy (RI), Ultra-Violet spectroscopy (UV), fluorescent analysis, radiochemical analysis, Near-InfraRed spectroscopy (Near-IR), Nuclear Magnetic Resonance spectroscopy (NMR), fluorescence spectroscopy, dual polarisation interferometry, computational methods, Light Scattering analysis (LS), gas chromatography (GC), or GC coupled with MS, direct injection (DI) coupled with LC-MS/MS and/or other methods or combination of methods known in the art.

The term "small molecule metabolites" includes organic and inorganic molecules which are present in the cell, cellular compartment, or organelle, usually having a molecular weight under 2,000, or 1,500. The small molecule metabolites of the cell are generally found free in solution in the cytoplasm or in other organelles, such as the mitochondria, where they form a pool of intermediates which can be metabolized further or used to generate large molecules, called macromolecules. The term "small molecule metabolites" includes signaling molecules and intermediates in the chemical reactions that transform energy derived from food into usable forms. Examples of small molecule metabolites include phospholipids, glycerophospholipids, lipids, plasmalogens, sugars, fatty acids, amino acids, nucleotides, intermediates formed during cellular processes, isomers and other small molecules found within the cell. In one embodiment, the small molecules of the invention are isolated. Preferred metabolites include lipids and fatty acids.

The term "subject" as used herein refers all members of the animal kingdom including mammals, preferably humans.

Overview

The present invention relates to the use metabolomic profiling in diagnosing and treating bacterial vaginosis (BV) in a female subject. The present invention relates also to individual or combination of biomarkers in diagnosing BV in a female subject.

BV is the most common vaginal condition, characterized by an increase in bacterial diversity with a corresponding decrease in *Lactobacillus* species. Clinical diagnosis often relies on microscopy, which may not reflect the microbiota composition accurately. In the present invention, novel biomarkers for BV have been identified, and demonstrate that the vaginal metabolome is strongly correlated with bacterial diversity. Furthermore, the organism responsible for producing γ-hydroxybutyrate (GHB) has been identified, and demonstrate production by this species in vitro. The present invention provides a new and inventive insight into the metabolism of the vaginal microbiota and provides for improved detection of disease.

The inventors have identified a number of metabolites as novel biomarkers of BV, in particular GHB and 2-hydroxyisovalerate (2HV). The novel biomarkers include GHB, methyl phosphate, 2-hydroxyisovalerate, 2-hydroxyglutarate, 5-aminovalerate, 2-hydroxyisocaproate, 2-hydroxy-3-methylvalerate, mannose-6-phosphate, 2-O-glycerol-d-galactopyranoside, beta-alanine, phenylethylamine, n-acetyl-putrescine.

As such, in one embodiment the present invention provides for a method of diagnosing BV in a subject, the method including detecting the presence of GHB and/or 2HV in an appropriate sample of the subject. The presence of GHB and/or 2HV in the sample being indicative of BV in the subject.

In another embodiment, the method of diagnosing BV in a subject may include detecting the level or amount or concentration (together referred to as "level") of at least one of GHB, 2HV, cadaverine, methyl phosphate, 2-hydroxyisovalerate, 2-hydroxyglutarate, putrescine, 5-aminovalerate, tyramine, 2-hydroxyisocaproate, 2-hydroxy-3-methylvalerate, mannose-6-phosphate, 2-O-glycerol-d-galactopyranoside, beta-alanine, phenylethylamine, n-acetyl-putrescine in a sample of the subject. The obtained level(s) of the at least one metabolites may be compared to the level(s) of these metabolites in a normal sample. A higher level of the at least one metabolites in the sample obtained from the subject relative to the normal sample is indicative that the subject has BV.

To circumvent the need of controlling the amount of sample, such as vaginal fluid, collected, the ratio of at least one of 2-HV and GHB to another metabolite in the sample may be calculated, for example, as ratios to the amino acid tyrosine. The ratio of GHB to tyrosine of about 0.6 or above may be indicative of BV diagnosis, i.e. 0.6, 0.7, 0.8, 09, 1, and anything in between, such as 0.620, 0.621, 0.623, 0.624, 0.625, 0.626, 0.627, 0.628, 0.629, 0.630 and so forth all the way to 1.000. The ratio of 2-HV to tyrosine of about 0.8 or above may be indicative of BV diagnosis, i.e., 0.8, 0.9, 1 and anything in between, such as 0.800, 0.801, 0.880, 0.881, 0.882, 0.883, 0.884, 0.885, 0.886, 0.887, 0.888, 0.889, 0.900 and so forth all the way to 1.000.

In another embodiment, the present invention is a method of diagnosing bacterial vaginosis (BV) in a female subject. The method of this embodiment may include: (a) obtaining an appropriate sample from the subject; and (b) obtaining a level of at least one metabolite in the sample and comparing the level of the at least one metabolite in the sample to the level of said at least one metabolite in a known normal sample (control sample), wherein the presence of the at least one metabolite in relatively higher levels than in the normal sample indicates BV diagnosis in the subject, and wherein the metabolite is selected from the group consisting of 2-hydroxyisovalerate (2HV), γ-hydroxybutyrate (GHB), cadaverine, methyl phosphate, 2-hydroxyglutarate, putrescine, 5-aminovalerate, tyramine, 2-hydroxyisocaproate, 2-hydroxy-3-methylvalerate, mannose-6-phosphate, 2-O-glycerol-d-galactopyranoside, beta-alanine, phenylethylamine and n-acetyl-putrescine.

Surprisingly, the inventors discovered that succinate is not significantly elevated in women with BV. As such, the method of the present invention may not need to (i.e. be free of) obtain the levels of succinate in the sample.

The vaginal sample may be obtained from a subject by a variety of known methods and can be analyzed with or without processing. Typically, the sample will be obtained by swab which can then be used to directly contact the sample with a test composition that facilitates detecting the presence of the metabolites in the sample, e.g., by immersing the swab in a liquid containing one or more of the test reagents or by rolling or otherwise contacting the swab with the surface of a test device, e.g., test strip, in or on which one or more of the test reagents are disposed. Another approach involves the immersion of the swab into a processing or extraction liquid, e.g., comprising buffers, preservatives, or the like, and removal of an aliquot of supernatant, either after filtration, centrifugation, or the like to remove particulate debris, or simply after allowing debris to settle by gravity. The aliquot of supernatant is then contacted with the test composition as above. In general, the method by which the sample is obtained and processed, if at all, is not critical and can be selected according to the particular needs or desires of the user. Yet another approach may involve a metabolome analysis of the sample. Since metabolites exist in a very broad range of concentrations and exhibit chemical diversity, there is no one instrument that can reliably measure all of the metabolites in the non-human or human metabolome in a single analysis. Instead, practitioners of metabolomic profiling generally use a suite of instruments, most often involving different combinations of liquid chromatography (LC) or gas chromatography (GC) coupled with MS, to obtain broad metabolic coverage [Circulation. 2012; 126: 1110-1120] Although in this invention NMR and Direct Injection LC-MS/MS (DI/LC-MS/MS) metabolic profiling were used, it should be understood that other instruments such as electrochemical analysis, RI, UV, near-IR, LS, GC and so forth may also be used.

The metabolic approach may also facilitate a diagnosis of BV in a subject by comparing the metabolic profile of a sample obtained from the subject, with the metabolic profile of a normal sample ("control").

The methods of the present invention may also increase the efficacy of the treatment of BV. A method of treating bacterial vaginosis (BV) in a patient, may include (a) obtaining a metabolic profile of the patient, (b) correlating each metabolite of the metabolic profile with a bacterium, and (c) administering the patient a drug or drugs that are effective against the correlated bacterium.

The present invention may also provide for a method of determining the efficacy of a BV treatment. A method of determining the efficacy of a bacterial vaginosis (BV) treatment in a patient undergoing BV treatment may include obtaining an appropriate sample of the patient at different stages of the treatment. For example, samples may be obtained when the patient was first diagnosed and at different time periods during the treatment of the patient. The levels of at least one of 2-hydroxyisovalerate (2HV) and γ-hydroxybutyrate (GHB) may be obtained in the samples at each one of those different stages. The levels of 2HV and/or GHB at each stage may then be compared. A general progressive decrease in the levels of 2HV and/or GHB along the different stages may be indicative of the efficacy of the treatment.

A method of determining the efficacy of a bacterial vaginosis (BV) treatment in a patient undergoing BV treatment may also include (a) obtaining an appropriate sample of the patient at different stages of the treatment; (b) obtaining the levels of at least one metabolite selected from the group consisting of 2-hydroxyisovalerate (2HV), γ-hydroxybutyrate (GHB), cadaverine, methyl phosphate, 2-hydroxyglutarate, putrescine, 5-aminovalerate, tyramine, 2-hydroxyisocaproate, 2-hydroxy-3-methylvalerate, mannose-6-phosphate, 2-O-glycerol-d-galactopyranoside, beta-alanine, phenylethylamine and n-acetyl-putrescine in the samples; and comparing the levels of the at least one metabolite in each stage. A general progressive decrease in the levels of 2HV and GHB along the different stages may be indicative of the efficacy of the treatment.

In addition to the previous embodiments, the present invention provides for: using metabolomics to determine efficacy of a treatment regime for BV; detecting asymptomatic subjects with BV, particularly assessing expecting mothers or maternal screening tests; diagnosing, prognosing or tailoring treatment of BV based on any or all of the identified BV biomarkers; using metabolomics to identify bacterial diversity—i.e. GHB correlates with pathogenic *G. vaginalis*, 2HV correlates with *Dialister, Prevotella, Atopobium*; using metabolomics to identify women at risk of pre-term birth or STD's; associating metabolomic signatures in BV with particular bacteria to identify microbial origin of particular metabolites.

In order to aid in the understanding and preparation of the within invention, the following illustrative, non-limiting, examples are provided.

EXAMPLES

Example 1

Materials and Methods
Clinical Samples

Premenopausal women between the ages of 18 and 55 were recruited at the University of Kigali Teaching Hospital (CHUK) and the Nyamata District Hospital in Rwanda. The Health Sciences Research Ethics Board at Western University, Canada, and the CHUK Ethics Committee, Rwanda granted ethical approval for the study. Participants were excluded if they had reached menopause, had a current infection of gonorrhoea, Chlamydia, genital warts, active genital herpes lesions, active syphilis, urinary tract infections, received drug therapy that may affect the vaginal microbiome, had unprotected sexual intercourse within the past 48 hours, used a vaginal douche, genital deodorant or genital wipe in past 48 hours, had taken any probiotic supplement in past 48 hours, or were menstruating at time of clinical visit. After reviewing details of the study, participants gave their signed consent before the start of the study. For metabolome analysis, sterile Dacron polyester-tipped swabs (BD) were pre-cut with sterilized scissors and weighed in 1.5 ml microcentrifuge tubes prior to sample collection. Using sterile forceps to clasp the pre-cut swabs, a nurse obtained vaginal samples for metabolomic analysis by rolling the swab against the mid-vaginal wall. A second full-length swab was obtained for Nugent Scoring and 16S rRNA gene sequencing using the same method. Nugent Scoring was performed at CHUK by Amy McMillan. Vaginal pH was measured using pH strips. Samples were frozen within 2 hours of collection and stored at −20° C. or below until analysis.
Microbiome Profiling Vaginal swabs for microbiome analysis were extracted using the QIAamp DNA stool mini kit (Qiagen) with the following modifications: swabs were vortexed in 1 mL buffer ASL before removal of the swab and addition of 200 mg of 0.1 mm zirconia/silica beads (Biospec Products). Samples were mixed vigorously for 2×30 seconds at full speed with cooling at room temperature between (Mini-BeadBeater; Biospec Products). After heating to 95° C. for 5 minutes, 1.2 ml of supernatant was aliquoted into a 2 ml tube and one-half an inhibitEx tablet (Qiagen) was added to each sample. All other steps were performed as per the manufacturers instructions. Sample amplification for sequencing was carried out using the forward primer (ACACTCTTTCCCTACACGACGCTCTTCCGATCTnnnn(8)CWACGCGARGAACCT TACC) and the reverse primer (CGGTCTCGGCATTCCTGCTGAACCGCTCTTCCGATCTn(12)ACRACACGAGCTG ACG AC) where nnnn indicates four randomly incorporated nucleotides, and (8) was a sample nucleotide specific barcode. The 5' end is the adapter sequence for the Illumina MiSeq sequencer and the sequences following the barcode are complementary to the V6 rRNA gene region. Amplification was carried out in 42 µL with each primer present at 0.8 pMol/mL, 20 µLGoTaq hot start colorless master mix (Promega) and 2 µL extracted DNA. The PCR protocol was as follows: initial activation step at 95° C. for 2 minutes and 25 cycles of 1 minute 95° C., 1 minute 55° C. and 1 minute 72° C.

All subsequent work was carried out at the London Regional Genomics Centre (LRGC, lrgc.ca, London, Ontario, Canada). Briefly, PCR products were quantified with a Qubit 2.0 Flourometer and the high sensitivity dsDNA specific fluorescent probes (Life Technologies). Samples were mixed at equimolar concentrations and purified with the QIAquick PCR Purification kit (QIAGEN). Samples were paired-end sequenced on an IlluminaMi-Seq with the 600 cycle version 3 reagents with 2×220 cycles. Data was extracted from only the first read, since it spanned the entirety of the V6 region including the reverse primer and barcode.

Resulting Reads were extracted and de-multiplexed using modifications of in-house Perl and UNIX-shell scripts with operational taxonomic units (OTUs) clustered at 97% identity, similar to our reported protocol (38). Automated taxonomic assignments were carried out by examining best hits from comparison the Ribosomal Database Project (rdp.cme.msu.edu) and manually curated by comparison to the Green genes database (greengenes.lbl.gov) and an in house database of vaginal sequences (Macklaim unpublished). Taxa with matches at least 95% similarity to query sequences were annotated as such. OTUs were summed to the genus level except for *lactobacilli*, and rare OTUs found at less than 0.5% abundance in any sample removed. Reads were deposited to the Short Read Archive (BioProject ID: PRJNA289672). To control for background contaminating sequences, a no-template control was also sequenced. Barplots were constructed with R {r-project.org} using proportional values.

To avoid inappropriate statistical inferences made from compositional data, centred log-ratios (clr), a method previously described by Aitchison (39) and adapted to microbiome data was used with paired t-tests for comparisons of genus and species level data (40). The Benjamini Hochberg (False Discovery rate) method was used to control for multiple testing with a significance threshold of 0.1. All statistical analysis, unless otherwise indicated, was carried out using R (r-project.org).
Sample Preparation GC-MS Vaginal swabs were pre-cut into 1.5 mL tubes and weighed prior to and after sample collection to determine the mass of vaginal fluid collected. After thawing, swabs were eluted in methanol-water (1:1) in 1.5 mL microcentrifuge tubes to a final concentration of 50 mg vaginal fluid/mL, which corresponded to a volume ranging from 200-2696 µL, depending on the mass of vaginal fluid collected. A blank swab eluted in 800 µL methanol-water was included as a negative control. All samples were vortexed for 10 s to extract metabolites, centrifuged for 5 min at 10 621 g, vortexed again for 10 s after which time the brushes were removed from tubes. Samples were centrifuged a final time for 10 min at 10 621 g to pellet cells and 200 μL of the supernatant was transferred to a GC-MS vial. The remaining supernatant was stored at '80° C. for LC-MS analysis. Next, 2 μL of 1 mg/mL ribitol was added to each vial as an internal standard. Samples were then dried to completeness using a SpeedVac. After drying, 100 μL of 2% methoxyamine-HCl in pyridine (MOX) was added to each vial for derivatization and incubated at 50° C. for 90 min. 100 μL N-Methyl-N-(trimethylsilyl) trifluoroacetamide (MSTFA) was then added and incubated at 50° C. for 30 min. Samples were then transferred to micro inserts before analysis by GC-MS (Agilent 7890A GC, 5975 inert MSD with triple axis detector). 1 μL of sample was injected using pulsed splitless mode into a 30 m DB5-MS column with 10 m duraguard, diameter 0.35 mm, thickness 0.25 μm (JNW Scientific). Helium was used as the carrier gas at a constant flow rate of 1 ml/min. Oven temperature was held at 70° C. for 5 min then increased at a rate of 5° C./min to 300° C. and held for 10 min. Solvent delay was set to 13 min to avoid solvent and a large lactate peak, and total run time was 61 min. Masses between 25 m/z and 600 m/z were selected by the detector. All samples were run in random order and a standard mix containing metabolites expected in samples was run multiple times throughout to ensure machine consistency.

Data Processing GC-MS

Chromatogram files were de-convoluted and converted to ELU format using the AMDIS Mass Spectrometry software (41), with the resolution set to high and sensitivity to medium. Chromatograms were then aligned and integrated using Spectconnect (42) (http://spectconnect.mit.edu), with the support threshold set to low. All metabolites found in the blank swab, or believed to have originated from derivatization reagents were removed from analysis at this time. After removal of swab metabolites, the IS matrix from Spectconnect was transformed using the additive log ratio transformation (alr) (39) and ribitol as a normalizing agent (log 2(x)/log 2(ribitol)). Zeros were replaced with two thirds the minimum detected value on a per metabolite basis prior to transformation. All further metabolite analysis was performed using these alr transformed values.

Metabolites were initially identified by comparison to the NIST 11 standard reference database (http://www.nist.gov/srd/nist1a.cfm). Identities of metabolites of interest were then confirmed by authentic standards if available.

Whole Metabolomic Analysis

In order to visualize trends in the metabolome as detected by GC-MS, principal component analysis (PCA) was performed using pareto scaling. To determine the percentage of variation in the metabolome that could be explained by a single variable we performed a series of partial least squares (PLS) regressions where each variable was used as a continuous latent variable. We tested every taxa, pH, Nugent score, pregnancy status, Shannon's diversity index and sample ID and compared the percent variation explained by the first component of each PLS. The variable with the highest value was determined to be most closely associated with the metabolome (Shannon's Diversity). Analysis was conducted in R using the PLS package and unit variance scaling. Jackknifing with 20% sample removal and 10 000 repetitions was then applied to determine 95% confidence intervals for each metabolite. Metabolites with confidence intervals that did not cross zero in both cohorts (pregnant and non-pregnant) were considered significantly associated with diversity. Heat maps of significant metabolites were constructed using the heatmap.2 function in R with average linkage hierarchical clustering and manhattan distances. Unless specified otherwise, all tests for differential metabolites between groups were performed using unpaired t-test with a Benjamini-Hochberg (False Discovery Rate) significance threshold of p<0.01 to account for multiple testing and multiple group comparisons. Correlations between metabolites and taxa were performed using alr transformed values for metabolites and clr values with 128 Monte Carlo instances for microbiota data in R using the ALDEx2 package (40). 16S rRNA microbial gene profiles generate compositional data that interferes with many standard statistical analyses, including deter determining correlations[26-28]. We used the aldex.corr function from the ALDEx2 package to calculate the Spearman's rank correlation between each OTU abundance in 128 inferred technical replicates and that were transformed by center log-ratio transform[27,28,49]. Spearman's rho values were converted to P values and corrected by the Benjamini-Hochberg procedure[52] using the cor.test function in R. This approach is conceptually similar to that adopted by SPARCC[26], but calculates the correlation between the OTU abundances and continuous metadata variables. Heatmaps of correlation p values were constructed using the heatmap.2 function in R with complete linkage hierarchical clustering and Euclidean distances."

Odds ratios of metabolites to identify Nugent BV from Normal were calculated from conditional logistic regressions performed on all metabolites using the glm function in R with 10 000 iterations and a binomial distribution. Metabolites with 95% CI>1 and p<0.01 (unpaired t-test, Benjamini-Hochberg corrected) were determined to be significantly elevated in Nugent BV. "Nugent BV" was defined by the clinical definition of a score of 7-10, with a score of 0-3 being "Nugent Normal". ROC curves and forest plots were built in R using the pROC and Gmisc packages respectively.

Sample Preparation LC-MS

To confirm GC-MS findings, samples which had at least 100 μL remaining after GC-MS were also analyzed by LC-MS. 100 μL of supernatant was transferred to vials with microinserts and directly injected into an Agilent 1290 Infinity HPLC coupled to a Q-Exactive mass spectrometer (Thermo Fisher Scientific) with a HESI source. For HPLC, 2 μL of each sample was injected into a ZORBAX Eclipse plus C18 2.1×50 mm×1.6 micron column. Mobile phase (A) consisted of 0.1% formic acid in water and mobile phase (B) consisted of 0.1% formic acid in acetonitrile. The initial composition of 100% (A) was held constant for 30 s and decreased to 0% over 3.0 min. Mobile phase A was then held at 0% for 1.5 minutes and returned to 100% over 30 s for a total run time of 5 min.

Full MS scanning between the ranges of m/z 50-750 was performed on all samples in both positive in negative mode at 140 000 resolution. The HESI source was operated under the following conditions: nitrogen flow of 25 and 15 arbitrary units for the sheath and auxiliary gas respectively, probe temperature and capillary temperature of 425° C. and 260° C. respectively and spray voltage of 4.8 kV and 3.9 kV in positive and negative mode respectively. The AGC target and maximum injection time were 3e6 and 500 ms respectively. For molecular characterization, every tenth sample was also analyzed with a data dependent $MS^2$ method where a 35 000 resolution full MS scan identified the top 10 signals above a 8.3e4 threshold which were subsequently selected at a 1.2 m/z isolation window for $MS^2$. Collision energy for $MS^2$ was 24, resolution 17 500, AGC target 1e5 and maximum injection time was 60 ms. Blanks of pure methanol were run between every sample to limit carryover, and a single sample was run multiple times with every batch to account for any machine inconsistency. A blank swab extract was also run as a negative control.

For increased sensitivity, a separate LC-MS method was used for relative quantification of GHB in human samples. This was accomplished by selected ion monitoring in the mass range of 103.1-107.1 m/z in positive mode, and integrating the LC peak area of the [M+H$^+$] ion (±5 ppm).

Data Processing LC-MS

After data acquisition Thermo .RAW files were converted to .MZML format using ProteoWizard (43) and imported into MZmine 2.11 (44) (http://mzmine.sourceforge.net) for chromatogram alignment and deconvolution. Masses were detected using the Exact Mass setting and a threshold of 1E5. For Chromatogram Builder, minimum time was 0.05 min, minimum height 3E3, and m/z threshold set to 0.025 m/z or 8 ppm. Chromatogram Deconvolution was achieved using the Noise Amplitude setting with the noise set to 5E4 and signal to 1E5 for negative mode. Due to an overall greater signal and noise in positive mode, the noise was adjusted to 6E5 and signal to 6.5E5 for positive mode. Join aligner was used to combine deconvoluted chromatograms into a single file with the m/z threshold set to 0.05 m/z or 10 ppm, weight for m/z and RT set to 20 and 10 respectively, and a RT tolerance of 0.4 min. After chromatograms were aligned, a single .CSV file was exported and all further analysis was carried out in R.

To confirm metabolites identified as significant by GC-MS in the LC-MS data set, the masses of metabolites of interest were searched in the LC-MS data set, and identities confirmed by MS$^2$ using METLIN (45) and the Human Metabolome Database (46) online resources. Standards of metabolites of interest were also run to confirm identities when available. An unpaired t-test with Benjamini-Hochberg correction was used to determine metabolites significantly different between Nugent BV and Normal in the LC-MS data set. Metabolites with corrected p<0.05 were considered statistically significant. Metabolites detected exclusively by LC-MS that have previously been associated with BV or health (lactate, trimethylamine) were also included in this analysis. Data was log base 10 transformed prior to data analysis and zeros replaced by ⅔ the minimum detected value on a per metabolite basis. To determine optimal cut points of biomarkers for diagnostic purposes, cut points were computed from LC-MS data using the OptimalCutpoints package in R (47) and the Youden Index method (48).

Validation in Blinded Replication Cohort

Women between the ages of 18 and 40 were recruited from an antenatal clinic at the Nyerere Dispensary in Mwanza, Tanzania as part of a larger study on the effect of micronutrient supplemented probiotic yogurt on pregnancy. The study was approved by both the Medical Research Coordinating Committee of the National Institute for Medical Research (NIMR), as well as from the Health Sciences Research Ethics Board at Western University. The study was registered with clinicaltrials.gov (NCT02021799). Samples were collected using the methods mentioned above, and Nugent scores performed by research technicians at NIMR in Mwanza, Tanzania. A subset of samples was selected based on these Nugent scores by a third party, who ensured there was not repeated sampling of any women. Amy McMillan, who performed metabolite analysis, was blinded to the Nugent scores for the duration of sample processing and data analysis. Biomarkers were quantified in samples by LC-MS using the protocols mentioned above. The study was unblinded after the submission of BV status based on the ratio cut points established in the Rwandan data set.

Identification of Putative GHB Dehydrogenases in *G. vaginalis* Strains

The protein sequence of a bona fide 4-hydroxybutyrate (GHB) dehydrogenase isolated from *Clostridium kluyveri* (25) (GI:347073) was blasted against all strains of *G. vaginalis* in the NCBI protein database. Blast results identified multiple isolates containing a putative protein with 44-46% identity to the GHB dehydrogenase from *C. kluyveri*. The strain used for in vitro experiments (*G. vaginalis* ATCC 14018) was not present in the NCBI protein database, however a nucleotide sequence in 14018 with 100% nucleotide identity to a putative 4-hydroxybutyrate dehydrogenases in strain ATCC 14019 (GI:311114893) was identified, indicating potential for GHB production by strain 14018.

In Vitro Extraction of GHB from Vaginal Isolates

Due to their fastidious nature, we found it difficult to obtain consistent growth of all vaginal strains in liquid media. To circumvent this, a lawn of bacteria was plated and metabolites were extracted from agar punches. All strains were grown on Columbia Blood Agar (CBA) plates using 5% sheep's blood for 96 h under strict anaerobic conditions, with the exception of *L. crispatus*, which was grown on de Man Rogosa Sharp (MRS) agar for 48 h. To extract metabolites, 16 agar punches 5 mm in diameter were taken from each plate and suspended in 3 mL 1:1 Me:H$_2$O. Samples were then sonicated in a water bath sonicater for 1 h, transferred to 1.5 ml tubes after vortexing and spun in a desktop microcentrifuge for 10 min at 10 621 g to pellet cells. 200 μl of supernatant was then aliquoted for GC-MS described above. The area of each peak was integrated using ChemStation (Agilent) by selecting m/z 233 in the range of 14-16 min. Initial peak width was set to 0.042 and initial threshold at 10. An authentic standard of GHB was run with samples to confirm identification. Un-inoculated media was used as a control and experiments were repeated three times with technical duplicates.

Results

The Vaginal Metabolome is Most Correlated with Bacterial Diversity

We completed a comprehensive untargeted metabolomic analysis of vaginal fluid in two cross-sectional cohorts of Rwandan women: pregnant (P, n=67) and non-pregnant (NP, n=64). To normalize the amount of sample collected, vaginal swabs were weighed prior to and after collection and normalized to equivalent concentrations. This enabled us to collect precise measurements of metabolites in vaginal fluid. Metabolite profiling was carried out using both gas chromatography-mass spectrometry (GC-MS) and liquid chromatography-mass spectrometry (LC-MS), and microbiota composition by 16S rRNA gene sequencing. The metabolome determined by GC-MS contained 128 metabolites. We conducted a series of partial least squares (PLS) regression analyses to determine the single variable that could best explain the variation in the metabolome. In both cohorts, the diversity of the microbiota, as measured using Shannon's Diversity (19), was the factor that explained the largest percent variation in the metabolome (Table 1), demonstrating that the vaginal metabolome is most correlated with bacterial diversity (FIG. 1A). Metabolites robustly associated with this diversity (95% CI< >0) (FIG. 1B) were determined by jackknifing, and within this group, metabolites associated with extreme diversity tended to have less variation in the jackknife replicates, and were common to both pregnant and non-pregnant women. This identified a core set of metabolites associated with diversity.

Figure 7:
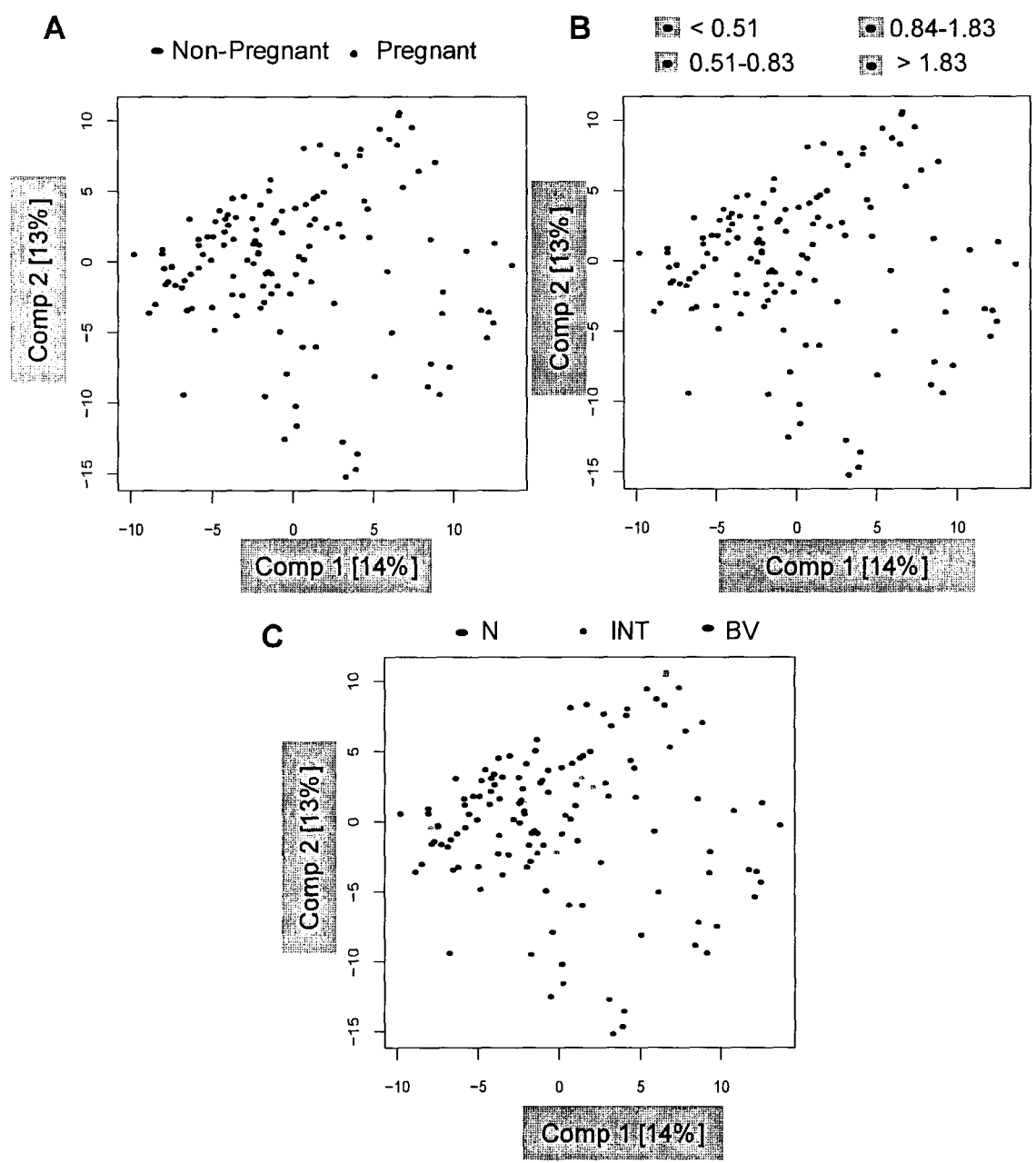
FIG. 7: Principal component analysis score plots. Points are colored according to (A) pregnancy status, (B) the diversity of the microbiota measured using the Shannon index, or (C) Nugent score.

The two cohorts overlapped by principal component analysis (PCA) (FIG. 7), and nometabolites were significantly different between pregnant and non-pregnant women (unpaired t-test, Benjamini-Hochberg p>0.01). Thus, the cohorts were combined for all further analysis.

Metabolites and Taxa Associated with Diversity

Figure 2:
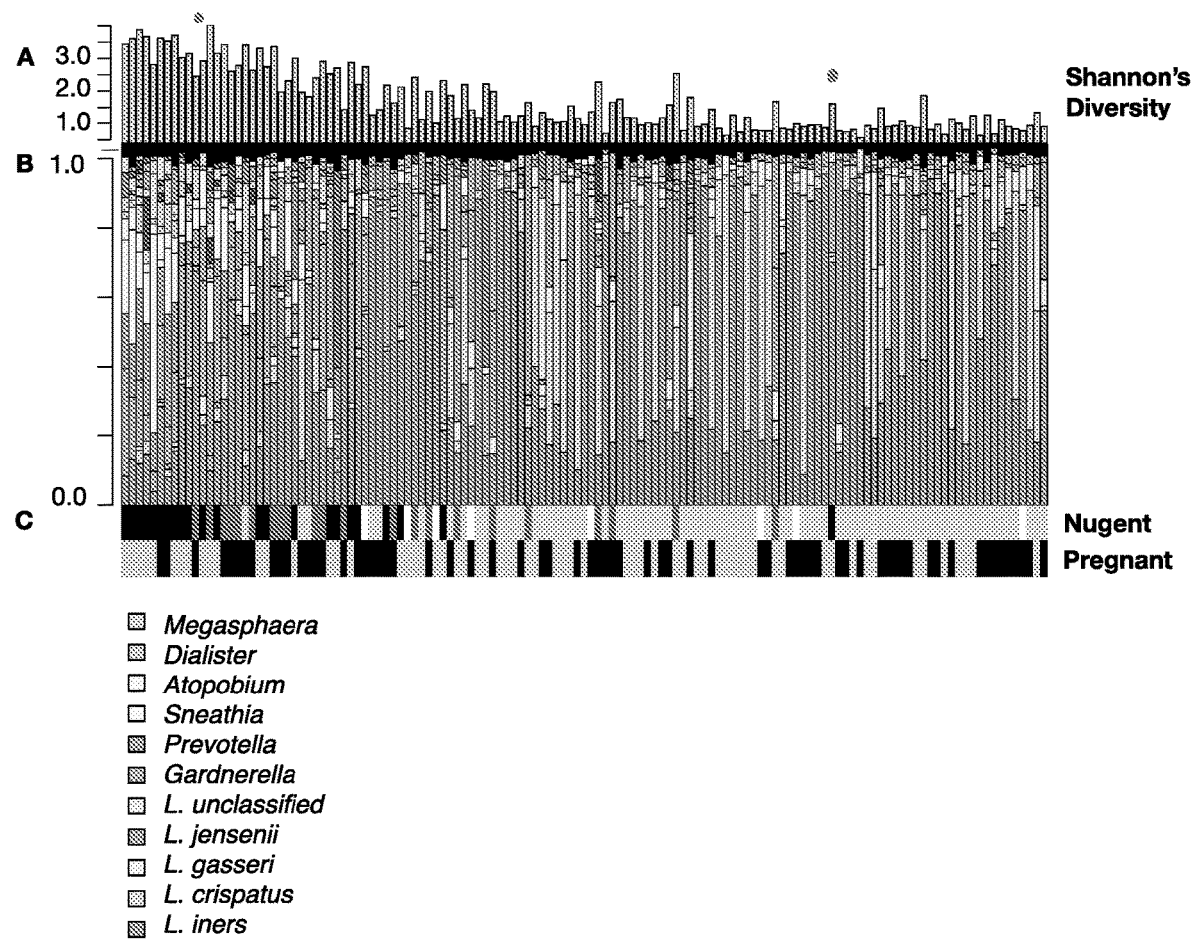
FIG. 2: Bacterial taxa and metabolites correlated with bacterial diversity in the vagina. Cohorts (non-pregnant and pregnant) were combined prior to analyses. Samples are ordered by their position on the first component (x-axis) of a partial least squares regression (PLS) built from metabolites using bacterial diversity as a continuous latent variable (see FIG. 8). Diversity was calculated using Shannon's diversity (A). The two dots indicate samples clearly misclassified by Nugent. Barplots (B) display the vaginal microbiota profiled using the V6 region of the 16S rRNA gene. Each bar represents a single sample from a single woman, and each colour a different bacterial taxa. The bacterial taxa listed on the right side of the barplots are (from top to bottom): *Megasphaera, Dialister, Atopobium, Sneathia, Prevotella, Gardnerella, L.* unclassified, *L. jensenii, L. gasseri, L. crispatus, L. iners.* (C) Nugent Score (black=7-10 (BV), dark grey=4-6 (Int), light grey=1-3 (N), white=ND) and pregnancy status (black=P, grey=NP). (D) Heatmap of GC-MS detected metabolites which were robustly associated with diversity in both cohorts (Jackknifing, 95% CI). Metabolites are clustered using average linkage hierarchical clustering. The listed metabolites are (from top to bottom): unknown 9, glutamate *, glycine *, inositol, aspartate *, leusine *, serine *, threonine *, threose, citrate, pyrimidine, tyrosine *, urea, glycerol-3-phosphate *, phenylalanine *, unknown sugar 1, unknown sugar 2, N-acetyl-lysine, ornithine, xylulose, alpha-ketoglutarate, phosphate sugar, lysine, putrescine *, 2H3M-valerate, thymine, unknown 11, unknown sugar 4, triethanolamine, unknown 22, unknown amine 1, tyramine *, cadaverine *, methyl phosphate, GHB *, 2-hydroxyisovalerate *, 2-hydroxyisocaproate *, unknown 4, mannose-6-phosphate *, 5-aminovalerate *, unknown amine 5, n-acetyl-putrescine, unknown amine 7, phenylethylamine *, unknown amine 4, unknown 2, gluconic acid, tryptophan, glucaric acid, aminomalonate, unknown 1, unknown sugar 8, phenyllactate, unknown sugar 5, glycerol-gulo-heptose, unknown amine 2. (E) Lactate and succinate abundance. From top to bottom: lactate *, succinate LC-MS *, succinate GC-MS *. (F) Color key and Histogram. Grey=ND. (*) indicates metabolites confirmed by authentic standards.
Figure 2:
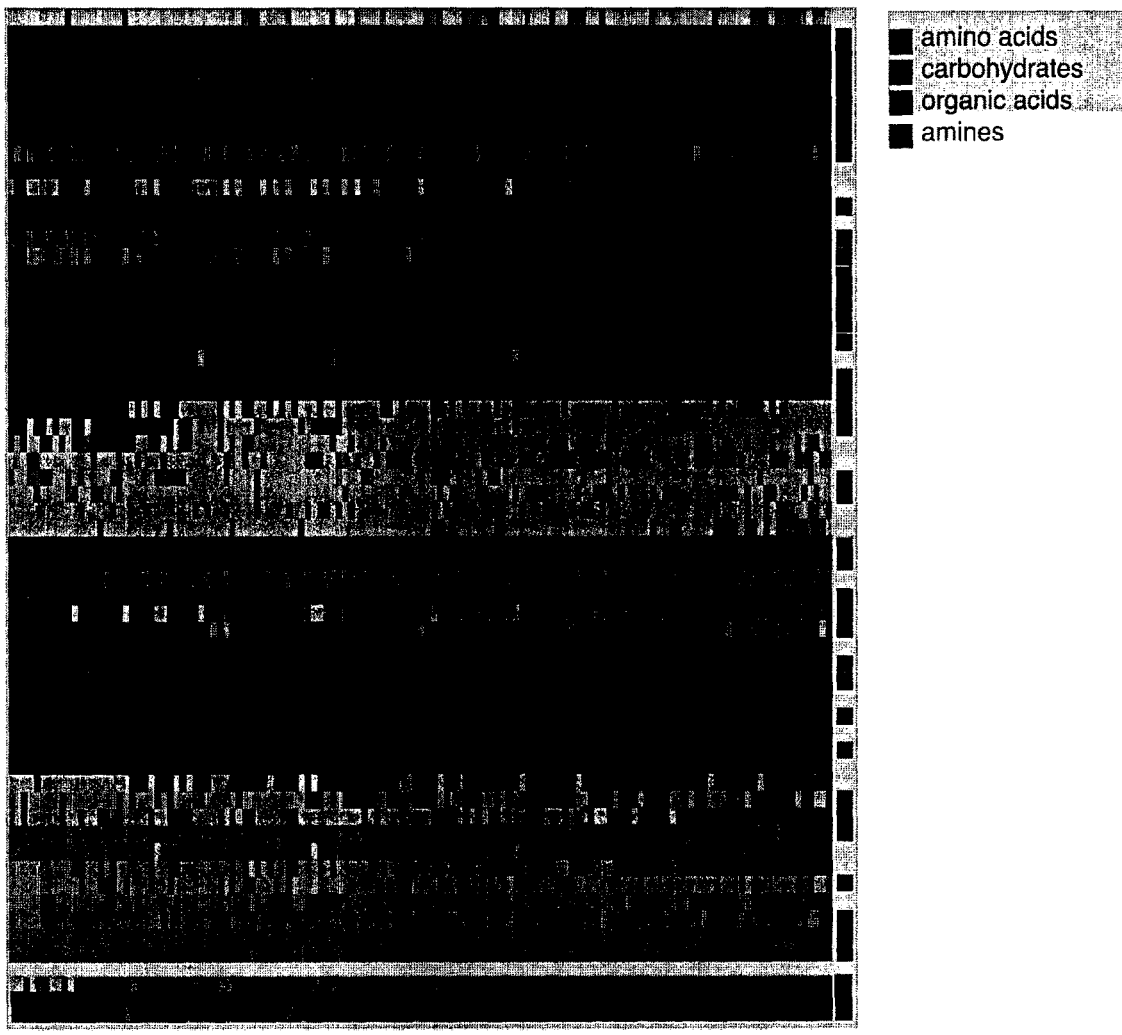
Figure 2:
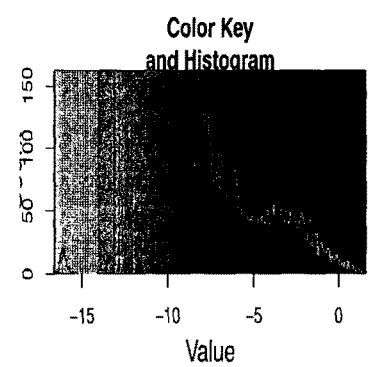
Figure 8:
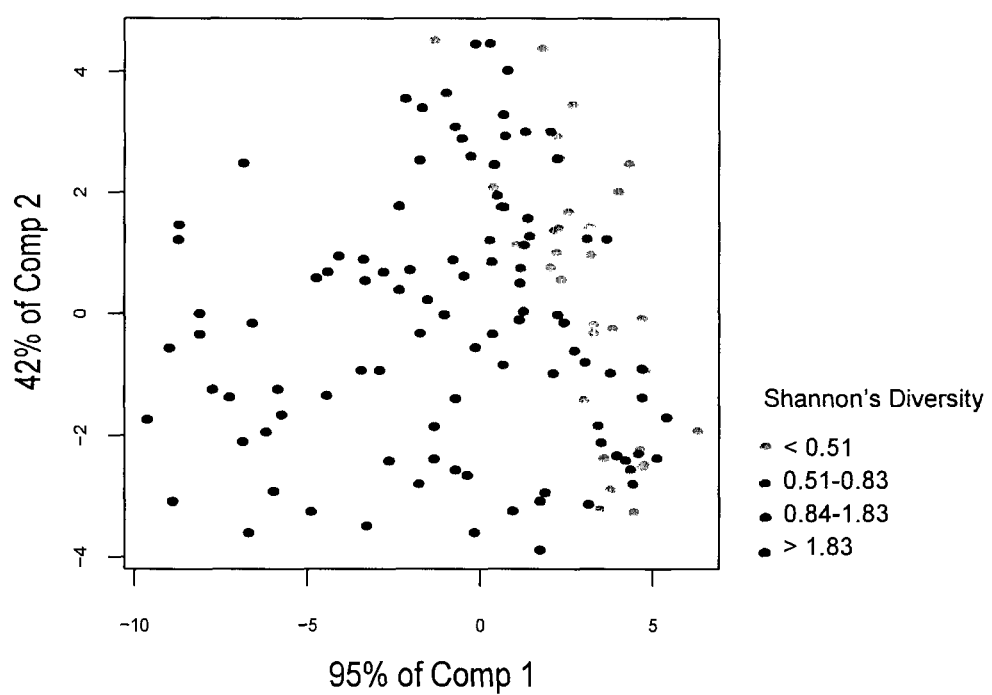
FIG. 8: Combined cohort PLS regression scoreplot. Each point represents a single woman (n=131). The position of points displays similarities in the metabolome, with samples closest to one another being most similar. Circles are colored by diversity of the microbiota measured using the Shannon Index, where darker circles indicate higher diversity.

A single PLS regression was performed on all samples with Shannon's diversity as a continuous latent variable (FIG. 8). Samples were then ordered by their position on the 1$^{st}$ component of this PLS. The diversity indices, microbiota and metabolites associated with diversity of PLS ordered samples are shown in FIG. 2. The vaginal microbiotas of Rwandan women were similar to women from other parts of the world, with the most abundant species being *L. iners* followed by *L. crispatus* (1-3,20) (FIG. 2B). Women with high bacterial diversity were dominated by a mixture of anaerobes, including *Gardnerella, Prevotella, Sneathia, Atopobium, Dialister* and *Megasphaera* species.

FIG. 2D displays metabolites robustly associated with bacterial diversity in both cohorts based on the PLS loadings in FIG. 1B. Metabolites associated with high diversity include amines, which contribute to malodor (16-18), and a number of organic acid derivatives such as 2-hydroxyisovalerate (2HV), γ-hydroxybutyrate (GHB), 2-hydroxyglutarate and 2-hydroxyisocaproate. Low diversity was characterized by elevated amino acids, including the amine precursors lysine, ornithine and tyrosine. Many of these metabolites were detected by LC-MS, and trimethylamine (high diversity) and lactate (low diversity) were detected exclusively by this method. The identities of metabolites of interest were confirmed with authentic standards when available (FIG. 2, asterisks).

Succinate is not Associated with Diversity or Clinical BV

Figure 9:
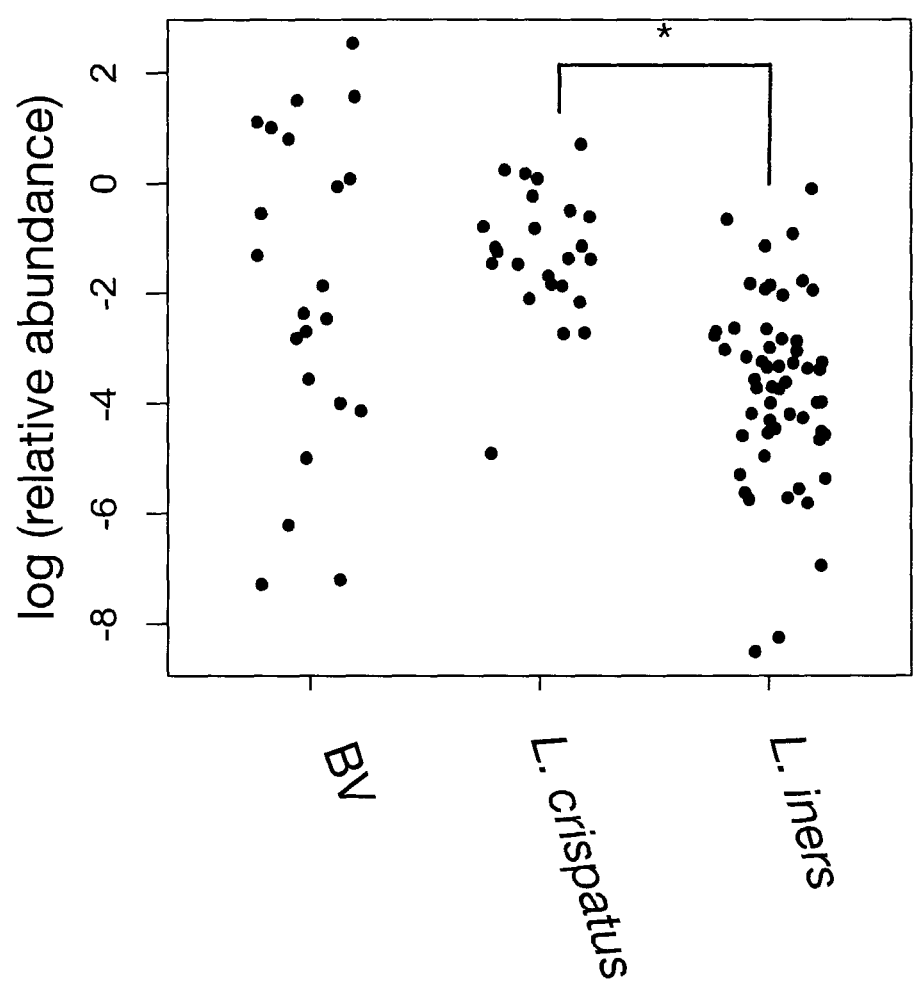
FIG. 9: Relative abundance of succinate in women dominated by *L. crispatus, L. iners* or Nugent BV detected by GC-MS (*) p<0.01, unpaired t-test, Benjamini-Hochberg corrected.

Succinate and lactate abundance are shown in panel E of FIG. 2. Succinate levels, and the succinate:lactate ratio have historically been associated with BV (21-23), and succinate has been postulated to play an immunomodulatory role (23). Here we show that succinate is not associated with bacterial diversity, nor is it significantly elevated in clinical BV as defined by Nugent scoring. This trend was independent of the detection method used. In addition, succinate was elevated in women dominated by *L. crispatus* compared with *L. iners* (unpaired t-test, Benjamini-Hochberg p<0.01) (FIG. 9), indicating *L. crispatus* may produce succinate in vivo, a phenomenon that has been demonstrated in vitro (24).

Metabolites Associated with Diversity are Sensitive and Specific for Clinical BV We defined clinical BV by the Nugent method, which is the current gold standard for BV diagnosis. This microscopy-based technique defines BV as a score of 7-10 when low numbers of *lactobacilli* morphotypes are observed, and high numbers of short rods presumed to represent BV associated bacteria are present. Nugent Normal (N) is defined as a score of 1-3, indicating almost exclusively *Lactobacillus* morphotypes. Intermediate samples are given a score of 4-6 and do not fit into either group. Although Nugent scores correlated well with bacterial diversity in our study, it was apparent from the microbiota and metabolome profiles that two samples (41 and 145) had been misclassified by Nugent (FIG. 2A, red dots). The Nugent status of these samples was therefore corrected prior to all further analyses.

Figure 3:
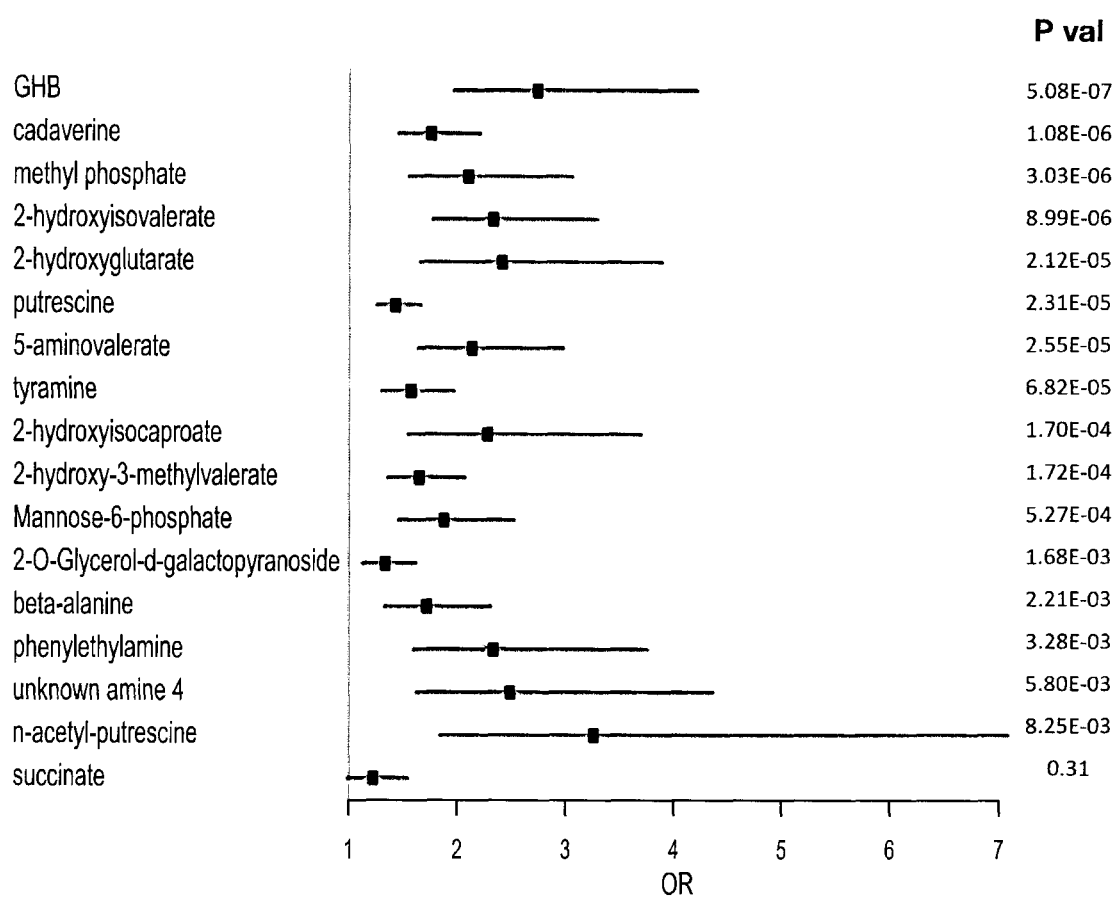
FIG. 3: Comparison of biomarkers to identify Nugent BV from Nugent N. (A) Odds ratios (OR) of metabolites with positive predictive value to identify Nugent BV. Bars represent 95% Confidence Intervals. Metabolites were detected by GC-MS and P values generated from unpaired t-tests with a Benjamini-Hochberg correction to account for multiple testing (p<0.01). (*) indicates metabolites confirmed by authentic standards. (B) Receiver operating characteristic (ROC) curves of metabolite ratios to identify Nugent BV from Nugent N. Ratios with largest area under the curve (AUC) are shown, along with succinate:lactate as a comparator. (C) AUC of selected metabolite ratios to identify Nugent BV. (D) AUC of metabolites alone to identify Nugent BV. Panels B-D were built from LC-MS data. GHB:γ-hyroxybutyrate, 2-HV:2-hydroxyisovalerate. [The arrows in (B) are only to help identify the curves.]
Figure 3:
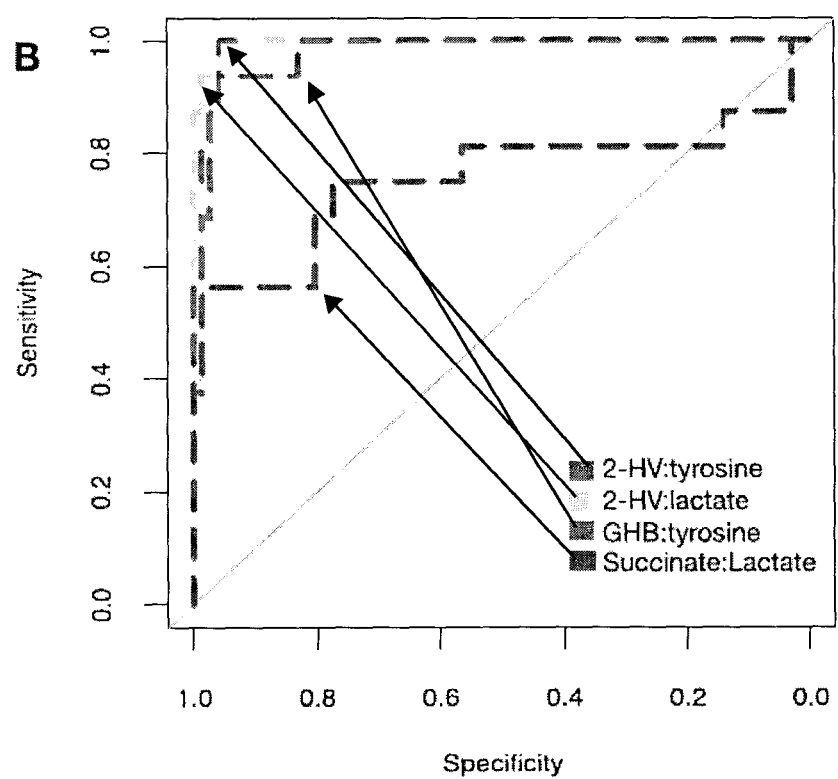

In total we identified 49 metabolites that were significantly different between BV and N (unpaired t-test, Benjamini-Hochberg p<0.01. Nineteen of these have not been reported as differential in the literature, and 12 could not be identified. We determined the odds ratio (OR) for BV based on conditional logistic regressions of all individual metabolites detected by GC-MS to determine if the metabolites we associated with high bacterial diversity could accurately identify clinical BV as defined by Nugent scoring. Metabolites significantly elevated in Nugent BV (unpaired t-test, Benjamini-Hochberg p<0.01) with OR>1 are shown in FIG. 3A. Succinate was included as a comparator, although it did not reach significance. Both GHB and 2HV were significantly higher in women with BV, and had OR>2.0, demonstrating they are novel indicators not only of high bacterial diversity, but also clinical BV. Receiver operating characteristics (ROC) curves built from LC-MS data determined that high 2HV, high GHB, low lactate and low tyrosine were the most sensitive and specific biomarkers for BV, with the largest area under the curve (AUC) achieved using the ratio of 2HV:tyrosine (AUC=0.993) (FIG. 3B-D). ROC curves of GC-MS data identified similar trends, with the largest AUC achieved by the ratio of GHB:tyrosine (AUC=0.968) (Table 2).

Figure 4:
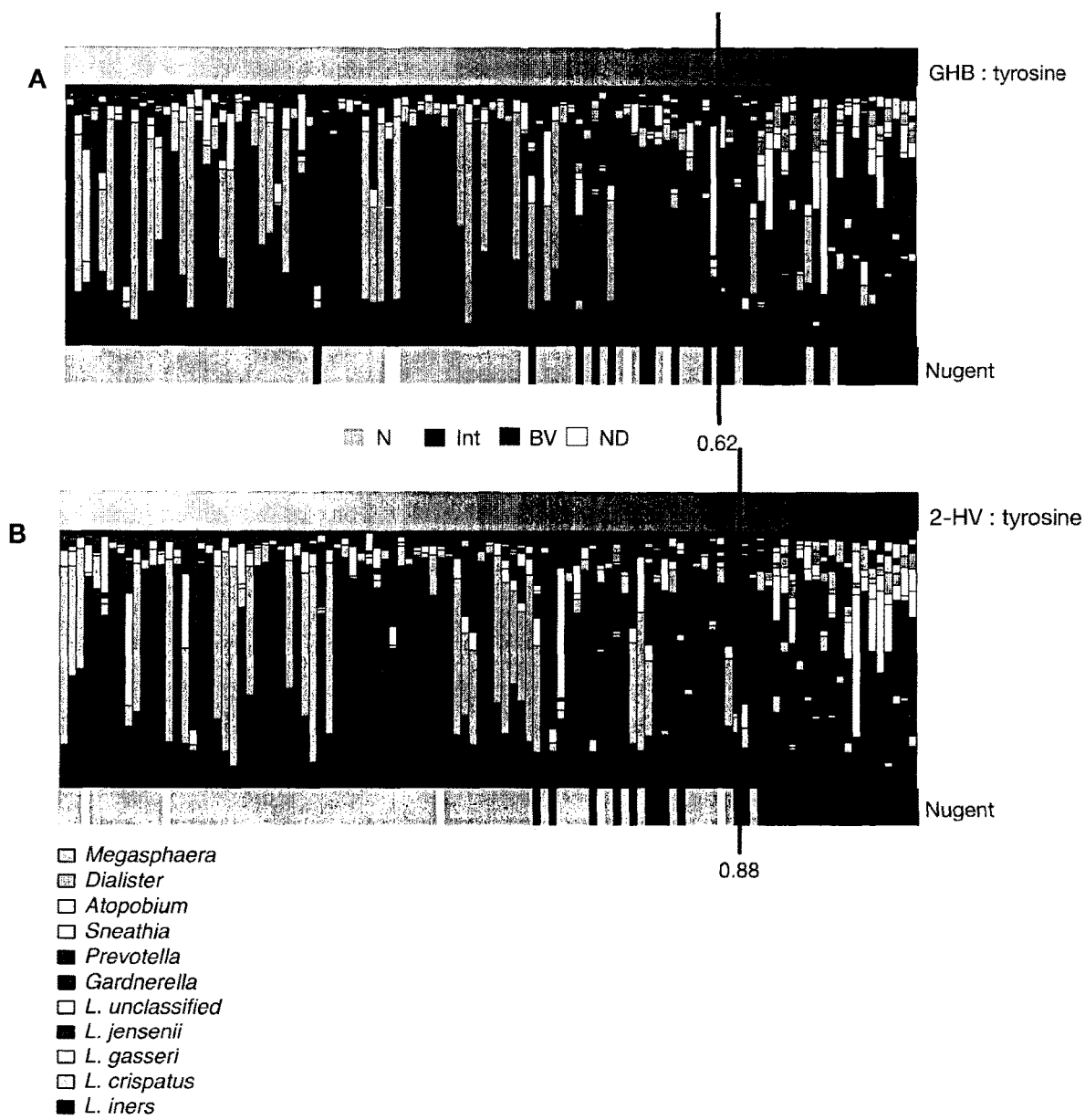
FIG. 4: Biomarker cut points effectively group Nugent Intermediate samples as BV or N. Barplots display the vaginal microbiota of Rwandan women sorted by (A) GHB:tyrosine or (B) 2HV:tyrosine. Each bar represents a single sample from a single woman and each colour a different bacterial taxa. Nugent scores are indicated below barplots. Black lines indicate ratio cut point for Nugent BV. Ratios were calculated from LC-MS data. The bacterial taxa listed on the right side of each (A) and (B) are (from top to bottom): *Megasphaera, Dialister, Atopobium, Sneathia, Prevotella, Gardnerella, L.* unclassified, *L. jensenii, L. gasseri, L. crispatus,* and *L. iners.*

We determined the optimal cut points for the GHB:tyrosine (0.621) and 2HV:tyrosine (0.882) ratios by selecting values which maximized the sensitivity and specificity for BV. Nugent intermediate samples grouped equally with N or BV based on these cut points, and intermediate-scored samples with smaller proportions of *lactobacilli* tended to group with BV (FIG. 4).

Validation of Biomarkers in a Blinded Replication Cohort from Tanzania

Figure 5:
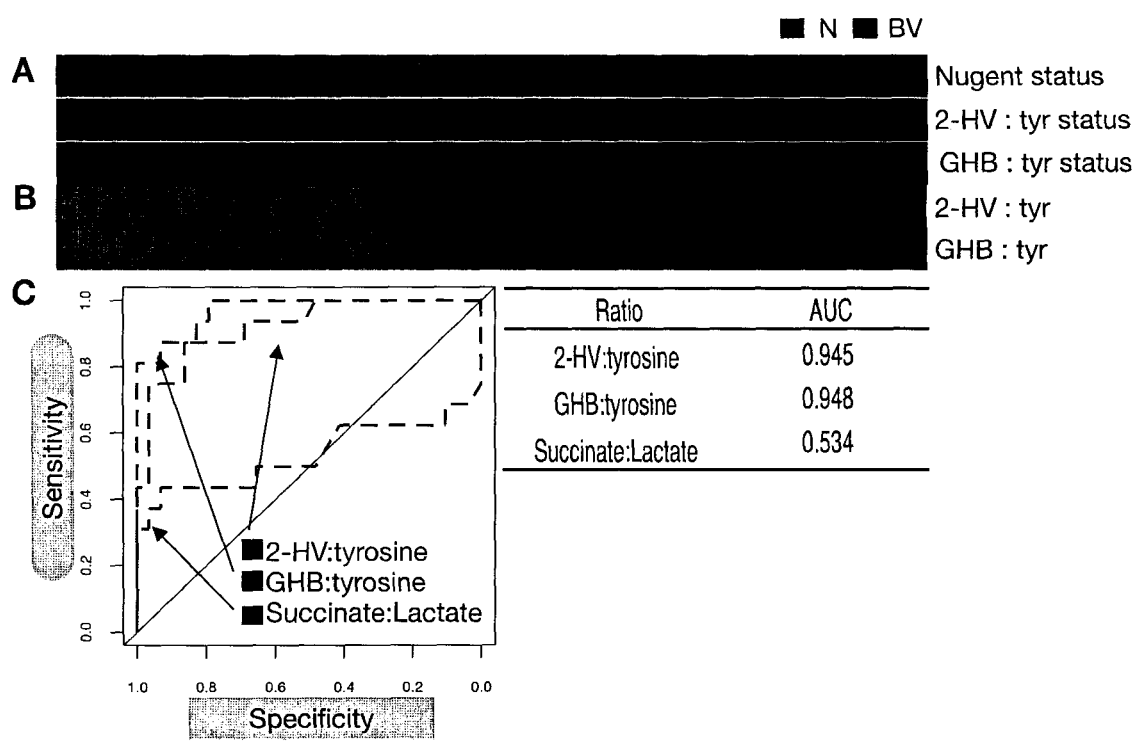
FIG. 5: Biomarker validation in a blinded replication cohort of 45 women from Tanzania. (A) BV status as defined by Nugent Score or ratio cut points identified in the Rwandan discovery data set. Black=BV, Gray=N. (B) Heatmap of ratio values. (C) ROC curves and (D) AUC of ratios to identify Nugent BV from N in the validation set. 2HV: 2-hydroxyisovalerate, GHB: γ-hydroxybutyrate, Tyr: tyrosine. [The arrows in (C) are only to help identify the curves.]

We validated these biomarkers in a blinded cohort of 45 pregnant women from Mwanza, Tanzania (Bisanz at al, manuscript submitted). Using the 2HV:tyrosine cut point identified in the Rwanda data set, we identified Nugent BV with 89% sensitivity and 94% specificity in the validation set (AUC=0.946), demonstrating our findings are reproducible in an ethnically distinct population (FIG. 5). The GHB:tyrosine ratio cutpoint was slightly less specific (88%), with an AUC of 0.948. We confirmed that succinate was not significantly different between Nugent N and BV in the validation set, nor was the succinate:lactate ratio.

Identification of *G. vaginalis* as a Producer of GHB

Figure 10:
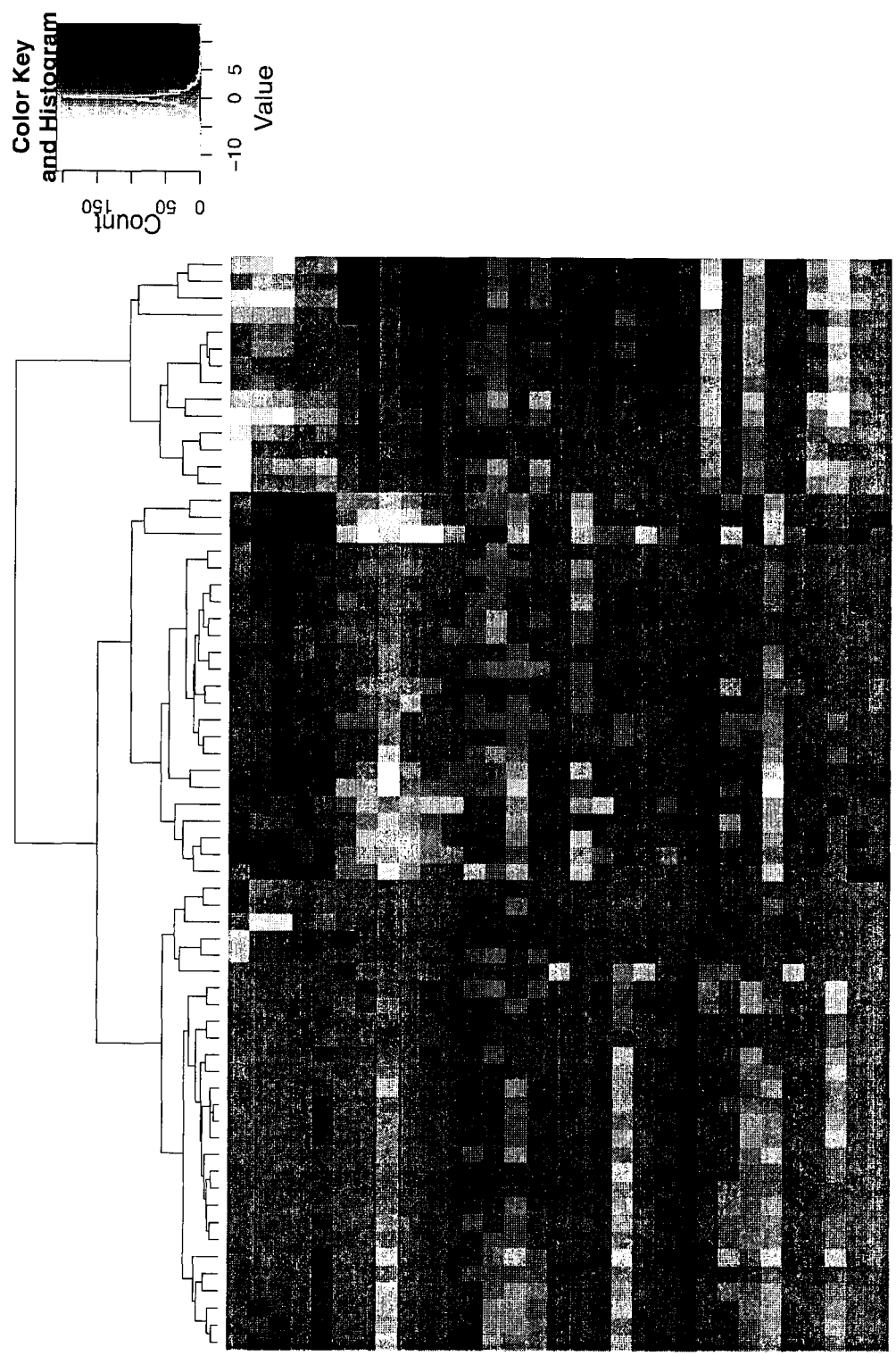
FIG. 10: Correlations between metabolites and taxa which are robust to random sampling of the underlying data. P values (Benjamini-Hochberg corrected) of Spearman's correlations are plotted on a log scale. The sign of each p value corresponds to the directionality of the correlation. Only metabolites and taxa for which any p values are <0.01 are displayed. List of Taxa (from top to bottom): *L. iners, L. crispatus, Lactobacillus* unclassified, *L. gasseri/johnsonii, L. jensenii, G. vaginalis, Prefotella, Sneathia, Atopobium, Dialister, Megasphaera, Bifidobacteriaceae, Streptococcus, Leptotrichiaceae, Bifidobacterium, Anaerococcus, Parvimonas, Viellonellaceae, Fusobacterium, Peptinophilus, Desulfotomaculum,* TM7, *Corynebacterium, Peptostreptococcus, Enterobacgteriaceae, Leptotrichia, Clostridiales*_IncertaeSedisXI, *Prevotellaceae, Enterobacteriaceae, Faecalibacterium* and *Clostriadiales*. Metabolites (from right to left): 2-hydroxyisovalerate, tyramine, cadaverine, GHB, unknown amine 4, phenylethylamine, unknown amine 5, n-acetyl-putrescine, putrescine, 5-aminovalerate, 2-hydroxyisocaproate, 2-hydroxyglutarate, unknown sugar 1, ornithine, unknown sugar 2, threonine, serine, glutamate, glycine, proline, leucine, unknown 1, asparate, phenyllactate, glycerol-gulo-heptose, unknown sugar 9, unknown 23, lysine, N-acetyl-lysine, tyrosine, unknown 2, a_ketoglurarate, G3P, phenylalanine, pyrimidine 1, glyceric_acid, citrate, malate, Mannose-6-phosphate, succinate, unknown 17, unknown amine 7, mannonate, allose, unknown amine 8, unkown 10, n-acetyl-galactosaminitol, unknown sugar 6, unknown 21, xylopyranose, ribofuranose, 1-phenyl-1,2-ehanediol, 1,2,4-butanetriol, unknown 14, propanal, unknown 8, beta-galactopyranoside, unknown 3, phosphate sugar, unknown amine 3, unknown amine 2, unknown amine 1.

Correlations between metabolites and the OTU abundances were performed using a method that took into account both the compositional nature of 16S rRNA gene survey data and the technical variation[40, 49, 50]. Metabolites and taxa which contained any correlation below a Benjamini-Hochberg corrected p<0.01 are displayed as a heatmap in FIG. 10. Correlations between metabolites and all taxa indicated that tyramine, putrescine, and cadaverine were most correlated with *Dialister* (Pearson's R=0.53, 0.58, 0.69, p<0.01) (Table 3), indicating this genus may contribute to malodor. We found that GHB was most correlated with *G. vaginalis* (Pearson's R=0.66, p<0.01), while 2HV was most correlated with *Dialister, Prevotella,* and *Atopobium* (Pearson's R=0.61, 0.58, 0.55, p<0.01).

Figure 6:
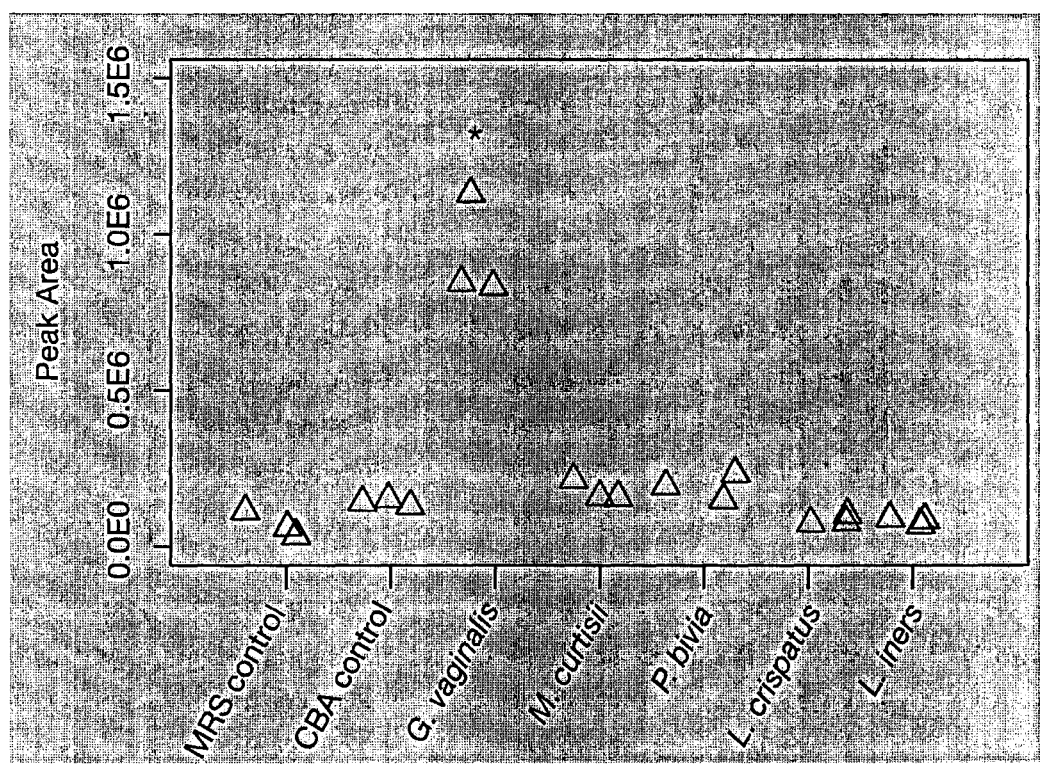
FIG. 6: Graph illustrating that GHB is produced by *Gardnerella vaginalis*. GHB was extracted from bacteria grown on agar plates and detected by GC-MS. Values from three independent experiments are shown where each point was generated from an average of technical duplicates. *p<0.05, unpaired t-test.

We chose to investigate the correlation between GHB and *G. vaginalis*, since this metabolite was novel, and predictive for both Shannon's diversity and Nugent BV. Examination of available genomes showed that many strains of *G. vaginalis* possess a putative GHB dehydrogenase (annotated as 4-hydroxybutyrate dehydrogenase). We extracted metabolites from bacterial colonies grown on agar plates and reproducibly detected GHB in *G. vaginalis* extracts well above control levels (unpaired t-test, p<0.05), but did not detect GHB from other species commonly associated with BV (FIG. 6, Table 4). These data suggest that *G. vaginalis* is the primary source of GHB detected in vivo.

TABLE 1

Percentage of variation in the metabolome that can be explained by a given variable. The percent variation explained by the x-axis (Component 1) of PLS regression plots are shown, where each variable was used as an independent continuous latent variable.

| Variable | Pregnant Comp1[%] | Non-Pregnant Comp1[%] |
|---|---|---|
| Shannon's Diversity | 9.081732 | 10.668774 |
| Nugent | 6.659424 | 10.235316 |
| pH | 6.089376 | 9.010365 |
| Lactobacillus | 6.985202 | 10.048794 |
| Gardnerella | 4.233945 | 4.41815541 |
| Prevotella | 6.69468 | 7.938502 |
| Atopobium | 5.324604 | 6.107562 |
| Dialister | 8.610902 | 6.247007 |
| Megasphaera | 3.72020232 | 4.61373 |
| Sample ID | 5.29943535 | 6.480972 |

TABLE 2

ROC area under the curve (AUC) of GC-MS detected metabolites to identify Nugent BV from N.

| metabolite or ratio | AUC |
|---|---|
| GHB/tyrosine | 0.968 |
| 2HV/tyrosine | 0.947 |
| high 2HV | 0.894 |
| high GHB | 0.893 |
| low tyrosine | 0.865 |
| high succinate | 0.61 |

TABLE 3

Correlation between metabolites of interest and bacterial taxa.

| 2HV | pearson.ecor | pearson.ep | pearson.eBH | spearman.erho | spearman.ep | spearman.eBH |
|---|---|---|---|---|---|---|
| Firmicutes; Negativicutes; Selenomonadales; Veillonellaceae; *Dialister* | 0.60600537 | 3.30E−14 | 1.68E−12 | 0.5558418 | 2.49E−12 | 1.27E−10 |
| Bacteroidetes; Bacteroidia; Bacteroidales; Prevotellaceae; *Prevotella* | 0.58520118 | 3.43E−13 | 8.76E−12 | 0.47777176 | 1.89E−08 | 3.91E−07 |
| Actinobacteria; Actinobacteria; Coriobacteriales; Coriobacteriaceae; *Atopobium* | 0.55115247 | 1.30E−11 | 2.20E−10 | 0.40488614 | 2.41E−06 | 2.82E−05 |
| Firmicutes; Clostridia; Clostridiales; Clostridiales_Family_XI_Incertae_Sedis (Peptostreptococcaceae); *Parvimonas* (*Peptostreptococcus*) | 0.45094202 | 1.66E−07 | 1.42E−06 | 0.32217156 | 0.00030583 | 0.00134817 |
| Actinobacteria; Actinobacteria; Bifidobacteriales; Bifidobacteriaceae; *Gardnerella* | 0.44166422 | 1.57E−07 | 1.40E−06 | 0.46946982 | 3.01E−08 | 5.42E−07 |
| Firmicutes; Negativicutes; Selenomonadales; Veillonellaceae; *Megasphaera* | 0.39089983 | 4.68E−06 | 2.94E−05 | 0.3023744 | 0.00052712 | 0.00211323 |
| Firmicutes; Negativicutes; Selenomonadales; Veillonellaceae; Veillonellaceae | 0.37174236 | 2.51E−05 | 0.00010284 | 0.33700568 | 0.0001313 | 0.00071769 |
| Firmicutes; Clostridia; Clostridiales; Peptococcaceae2; *Desulfotomaculum* | 0.37007616 | 2.36E−05 | 0.00010372 | 0.29997444 | 0.00074616 | 0.00281363 |
| Fusobacteria; Fusobacteria; Fusobacteriales; Leptotrichiaceae; *Sneathia* | 0.3536948 | 3.76E−05 | 0.00015414 | 0.12690735 | 0.15108217 | 0.24478806 |
| Fusobacteria; Fusobacteria; Fusobacteriales; Leptotrichiaceae; *Leptotrichia* | 0.2708063 | 0.00241089 | 0.00574113 | 0.09456653 | 0.300704 | 0.40623705 |
| Bacteroidetes; Bacteroidia; Bacteroidales; Porphyromonadaceae; *Porphyromonas* | 0.26170159 | 0.00323878 | 0.00748742 | 0.14766672 | 0.10111267 | 0.17484295 |
| Bacteroidetes; Bacteroidia; Bacteroidales; Porphyromonadaceae; Porphyromonadaceae | 0.25281914 | 0.00910214 | 0.01647803 | 0.20323819 | 0.03023195 | 0.06363619 |
| Fusobacteria; Fusobacteria; Fusobacteriales; Leptotrichiaceae; unclassified | 0.2516436 | 0.00396966 | 0.00914982 | 0.05551792 | 0.53164273 | 0.61641743 |
| Firmicutes; Clostridia; Clostridiales; Clostridiales_IncertaeSedisXI; *Peptoniphilus* | 0.23179266 | 0.00849663 | 0.01692367 | 0.23958014 | 0.00680074 | 0.02031086 |
| Firmicutes; Clostridia; Cloridiales; Lachnospiraceae; *Butyrivibrio* | 0.22872429 | 0.01263764 | 0.02312852 | 0.20320574 | 0.03237024 | 0.06687424 |
| Firmicutes; Clostridia; Clostridiales; Clostridiales_IncertaeSedisXI; unclassified | 0.20170051 | 0.02563534 | 0.04283972 | 0.14991939 | 0.09932141 | 0.17179193 |
| Firmicutes; Lactobacillales; Carnobacteriaceae (Aerococcaceae); Granulicatella (Aerococcaceae); unclassified | 0.1909414 | 0.03160352 | 0.0519773 | 0.18464979 | 0.03985809 | 0.08313279 |
| Firmicutes; Clostridia; Clostridiales; Lachnospiraceae; *Moryella* | 0.16271101 | 0.09812866 | 0.13314892 | 0.08837221 | 0.34523292 | 0.44094065 |
| Firmicutes; Clostridia; Clostridiales; unclassified; BVAB1_2_3 | 0.15466494 | 0.08167386 | 0.11854945 | 0.09094375 | 0.30933594 | 0.41958272 |
| Firmicutes; Clostridia; Clostridiales; Peptostreptococcaceae; *Peptostreptococcus* | 0.1433522 | 0.11140973 | 0.15506989 | 0.04820462 | 0.59347812 | 0.66109539 |

TABLE 3-continued

Correlation between metabolites of interest and bacterial taxa.

| 2HV | pearson.ecor | pearson.ep | pearson.eBH | spearman.erho | spearman.ep | spearman.eBH |
|---|---|---|---|---|---|---|
| Firmicutes; Negativicutes; Selenomonadales; Veillonellaceae; *Veillonella* | 0.10012567 | 0.26056142 | 0.33133115 | −0.0576918 | 0.51937668 | 0.60701457 |
| Actinobacteria; Actinobacteria; Bifidobacteriales; Bifidobacteriaceae; unclassified | 0.04472732 | 0.61348571 | 0.69187443 | −0.0340811 | 0.70090314 | 0.74633715 |
| Firmicutes; Bacilli; Bacillales; Bacillaceae2; unclassified | 0.02750373 | 0.60754259 | 0.67194214 | 0.01901891 | 0.63800934 | 0.6959755 |
| Fusobacteria; Fusobacteria; Fusobacteriales; Fusobacteriaceae; *Fusobacterium* | 0.00230961 | 0.74188668 | 0.79375836 | −0.0660609 | 0.46554219 | 0.55875019 |
| Bacteroidetes; Bacteroidia; Bacteroidales; Prevotellaceae; unclassified | −0.0015177 | 0.83917508 | 0.874238 | −0.0752092 | 0.41519891 | 0.51194294 |
| Actinobacteria; Actinobacteria; Actinomycetales; Actinomycetaceae; *Mobiluncus* | −0.0052748 | 0.70824909 | 0.7656668 | −0.0159685 | 0.7259052 | 0.76495548 |
| Firmicutes; Clostridia; Clostridiales; Clostridiales_IncertaeSedisXI; *Anaerococcus* | −0.0108045 | 0.87674243 | 0.90692694 | 0.03710047 | 0.67770614 | 0.73135001 |
| seq_57; Other; Other; Other; Other | −0.0178778 | 0.66164055 | 0.71730195 | −0.0767538 | 0.41447985 | 0.50132278 |
| Bacteriodetes; Bacterodia; Bacteroidales; Bacteroidaceae; *Bacteroides* | −0.0381615 | 0.6039972 | 0.66268255 | −0.0722071 | 0.4531136 | 0.53497274 |
| TM7; unclassified; unclassified; unclassified; TM7 | −0.0413976 | 0.5922482 | 0.64996375 | 0.0565856 | 0.53065842 | 0.60316577 |
| Firmicutes; Clostridia; Clostridiales; Lachnospiraceae; unclassified | −0.0521789 | 0.56297081 | 0.63134146 | −0.0575071 | 0.52714164 | 0.60686547 |
| Tenericutes; Mollicutes; Mycoplasmatales; Mycoplasmataceae; *Mycoplasma* | −0.1020763 | 0.29841606 | 0.36222553 | −0.058314 | 0.52400508 | 0.60401022 |
| Firmicutes; Bacilli; Lactobacillales; Enterococcaceae; unclassified | −0.116099 | 0.23111984 | 0.28990062 | −0.1368121 | 0.14732187 | 0.22808267 |
| Firmicutes; Clostridia; Clostridiales; Clostridiales_IncertaeSedisXI; *Finegoldia* | −0.1562279 | 0.09318734 | 0.13003396 | −0.1076125 | 0.23313946 | 0.336017 |
| Firmicutes; Clostridia; Clostridiales; unclassified; Clostridiales | −0.163697 | 0.10159311 | 0.13726306 | −0.1242001 | 0.19171111 | 0.27875721 |
| Proteobacteria; Gammaproteobacteria; Enterobacteriales; Enterobacteriaceae; *Proteus* | −0.1712075 | 0.12770933 | 0.16355187 | −0.1476057 | 0.18714704 | 0.24966143 |
| Firmicutes; Clostridia; Clostridiales; Lachnospiraceae; *Roseburia* | −0.1729021 | 0.09080287 | 0.12363059 | −0.1386541 | 0.16186543 | 0.23799918 |
| Firmicutes; Clostridia; Clostridiales; Ruminococcaceae; *Faecalibacterium* | −0.1895158 | 0.06208835 | 0.08741935 | −0.2033432 | 0.03159267 | 0.06541593 |
| Firmicutes; Bacilli; Bacillales; Paenibacillaceae1; *Paenibacillus* | −0.1974775 | 0.06413735 | 0.08890124 | −0.1503821 | 0.13368065 | 0.2034887 |
| Bacteroidetes; Bacteroidia; Bacteroidales; Prevotellaceae; Prevotellaceae | −0.2080327 | 0.02789232 | 0.04441215 | −0.2374581 | 0.00876974 | 0.02407996 |
| Actinobacteria; Actinobacteria; Bifidobacteriales; Bifidobacteriaceae; *Bifidobacterium* | −0.2266473 | 0.01000771 | 0.01926518 | −0.1947268 | 0.02830751 | 0.06381711 |
| Bacteroidetes; Bacteroidia; Bacteroidales; Bacteroidaceae; *Bacteroides* | −0.2357637 | 0.022893 | 0.03536374 | −0.2297873 | 0.01636784 | 0.03746771 |
| Firmicutes; Bacilli; Lactobacillales; Streptococcaceae; *Streptococcus* | −0.2522641 | 0.00394012 | 0.00891408 | −0.1543695 | 0.08115439 | 0.1481308 |
| Proteobacteria; Gammaproteobacteria; Enterobacteriales; Enterobacteriaceae; *Escherichia/Shigella* | −0.2958338 | 0.0014534 | 0.00356496 | −0.3208459 | 0.00029098 | 0.0012858 |
| Firmicutes; Bacilli; Lactobacillales; Lactobacillaceae; Lactobacillus_gasseri/johnsonii | −0.3115115 | 0.00030724 | 0.00096953 | −0.1956684 | 0.02603087 | 0.05983535 |
| Firmicutes; Bacilli; Lactobacillales; Lactobacillaceae; Lactobacillus_jensenii | −0.3139858 | 0.00027365 | 0.00088583 | −0.2082727 | 0.01766795 | 0.04491276 |
| Actinobacteria; Actinobacteria; Actinomycetales; Corynebacteriaceae; *Corynebacterium* | −0.3387363 | 0.00010832 | 0.00038102 | −0.3188516 | 0.00028539 | 0.00129783 |
| Proteobacteria; Gammaproteobacteria; Enterobacteriales; Enterobacteriaceae; unclassified | −0.3429449 | 0.00037438 | 0.00098664 | −0.3811172 | 1.50E−05 | 0.00011986 |
| Firmicutes; Bacilli; Lactobacillales; Lactobacillaceae; Lactobacillus_iners | −0.3600745 | 2.62E−05 | 0.00011595 | −0.305816 | 0.00043474 | 0.00178995 |
| Firmicutes; Bacilli; Lactobacillales; Lactobacillaceae; Lactobacillus_crispatus | −0.3831506 | 6.65E−06 | 3.95E−05 | −0.3248793 | 0.00017464 | 0.00094937 |
| Firmicutes; Bacilli; Lactobacillales; Lactobacillaceae; *Lactobacillus* | −0.4913617 | 2.99E−09 | 3.78E−08 | −0.379802 | 9.90E−06 | 9.07E−05 |

TABLE 4

Bacterial strains used for in vitro experiments.

| Strain | Source |
| --- | --- |
| L. iners AB-1 | isolated from the vagina of a healthy woman |
| L. crispatus 33820 | ATCC |
| P. bivia ATCC 29303 | ATCC |
| G. vaginalis 14018 | ATCC |
| M. curtisii 35241 | ATCC |
| A. vaginae | isolated from the vagina of a woman with BV |

Discussion

The present invention demonstrates that the vaginal metabolome is strongly correlated with bacterial diversity in both pregnant and non-pregnant Rwandan women, and identified 2HV and GHB as novel biomarkers of clinical BV, the latter of which we attribute to production by G. vaginalis. We obtained extremely accurate results by controlling for the mass of vaginal fluid collected, however we recognize this may not be logistically possible in a clinical setting. To circumvent this need we expressed biomarkers as ratios to the amino acid tyrosine, the most differential amino acid in health. Given the highly conserved nature of the vaginal microbiota across different populations and ethnicities (1-3, 20), we expect these biomarkers to be globally applicable for the diagnosis of BV, and our ability to replicate findings in a distinct population strongly supports this theory.

The finding that succinate, an end product of anaerobic respiration, was not significantly elevated in women with BV was an unexpected outcome. This metabolite has historically been associated with the condition, but has not been tested in the context of a large untargeted metabolomic study. Other groups have reported large ranges in succinate abundance in women with BV (21,22), or used pooled samples (22).

In addition to GHB, 2HV was identified as a highly specific novel biomarker for BV. 2HV is produced from breakdown of branched chain amino acids in humans (28) and some bacteria (29-31). When the trend for amino acid depletion in BV is considered, these findings suggest increased amino acid catabolism in this condition. Some of these amino acids are converted to the amines cadaverine, tyramine, and putrescine, which are also associated with BV. These odor-causing compounds were most correlated with Dialister. Yeoman et al. (32) also linked amines to Dialister species, and the decarboxylating genes required for amine production are expressed by this genus in vivo (27). These data strongly suggest that Dialister is one of the genera responsible for malodor in the vagina. Given the small proportion of this genus in women with BV (0.2-8% in our study), this emphasizes the need for functional characterizations of the microbiome using metabolomic and transcriptomic approaches.

Using an untargeted metabolomics approach, we identify novel biomarkers for BV in a cohort of 131 Rwandan women, and demonstrate that metabolic products in the vagina are closely associated with bacterial diversity. Metabolites associated with high diversity and clinical BV includes 2-hydroxyisovalerate and γ-hydroxybutyrate (GHB), but not the anaerobic end-product succinate, while low diversity is characterized by lactate and amino acids. These biomarkers are independent of pregnancy status, and were validated in a blinded replication cohort from Tanzania (n=45), in which we predicted clinical BV with 91% accuracy. Correlations between the metabolome and microbiota identified Gardnerella vaginalis as a putative producer of one of these compounds, GHB, and we demonstrate production by this species in vitro. This work provides novel insight into the metabolism of the vaginal microbiota and identifies highly specific biomarkers for a common condition.

REFERENCES

1. Ravel J, et al (2011) Vaginal microbiome of reproductive-age women. Proc Natl Acad Sci USA 108 Suppl 1: 4680-4687.
2. Hummelen R, et al (2010) Deep sequencing of the vaginal microbiota of women with HIV. PLoS One 5(8): e12078.
3. Fredricks D N, Fiedler T L & Marrazzo J M (2005) Molecular identification of bacteria associated with bacterial vaginosis. N Engl J Med 353(18): 1899-1911.
4. Koumans E H, et al (2007) The prevalence of bacterial vaginosis in the united states, 2001-2004; associations with symptoms, sexual behaviors, and reproductive health. Sex Transm Dis 34(11): 864-869.
5. Klebanoff M A, et al (2004) Vulvovaginal symptoms in women with bacterial vaginosis. Obstet Gynecol 104(2): 267-272.
6. Sobel J D, Karpas Z & Lorber A (2012) Diagnosing vaginal infections through measurement of biogenic amines by ion mobility spectrometry. Eur J Obstet Gynecol Reprod Biol. 163(1):81-4.
7. Wolrath H, Forsum U, Larsson P G & Boren H (2001) Analysis of bacterial vaginosis-related amines in vaginal fluid by gas chromatography and mass spectrometry. J Clin Microbiol 39(11): 4026-4031.
8. Wolrath H, Stahlbom B, Hallen A & Forsum U (2005) Trimethylamine and trimethylamine oxide levels in normal women and women with bacterial vaginosis reflect a local metabolism in vaginal secretion as compared to urine. Apmis 113(7-8): 513-516.
9. Sha B E, et al (2005) Female genital-tract HIV load correlates inversely with Lactobacillus species but positively with bacterial vaginosis and mycoplasma hominis. J Infect Dis 191(1): 25-32.
10. Das T R, Jahan S, Begum S R & Akhtar M F (2011) Association between bacterial vaginosis and preterm delivery. Mymensingh Med J 20(1): 115-120.
11. Nugent R P, Krohn M A & Hillier S L (1991) Reliability of diagnosing bacterial vaginosis is improved by a standardized method of gram stain interpretation. J Clin Microbiol 29(2): 297-301.
12. Amsel R, et al (1983) Nonspecific vaginitis. diagnostic criteria and microbial and epidemiologic associations. Am J Med 74(1): 14-22.
13. Chaijareenont K, Sirimai K, Boriboonhirunsarn D & Kiriwat O (2004) Accuracy of Nugent's score and each Amsel's criteria in the diagnosis of bacterial vaginosis. J Med Assoc Thai 87(11): 1270-1274.
14. Sha B E, et al (2005) Utility of amsel criteria, nugent score, and quantitative PCR for Gardnerella vaginalis, Mycoplasma hominis, and Lactobacillus spp. for diagnosis of bacterial vaginosis in human immunodeficiency virus-infected women. J Clin Microbiol 43(9): 4607-4612.
15. Schwebke J R, Hillier S L, Sobel J D, McGregor J A & Sweet R L (1996) Validity of the vaginal gram stain for the diagnosis of bacterial vaginosis. Obstet Gynecol 88(4 Pt 1): 573-576.

16. Mayers J R, et al (2014) Elevation of circulating branched-chain amino acids is an early event in human pancreatic adenocarcinoma development *Nat Med* 20(10): 1193-1198.
17. Sreekumar A, et al (2009) Metabolomic profiles delineate potential role for sarcosine in prostate cancer progression. *Nature* 457(7231): 910-914.
18. Theriot C M, et al (2014) Antibiotic-induced shifts in the mouse gut microbiome and metabolome increase susceptibility to *Clostridium difficile* infection. *Nat Commun* 5: 3114.
19. Shannon C E (1997) The mathematical theory of communication. 1963. *MD Comput* 14(4): 306-317.
20. Zhou X, et al (2010) The vaginal bacterial communities of Japanese women resemble those of women in other racial groups. *FEMS Immunol Med Microbiol* 58(2): 169-181.
21. Ison C A, Easmon C S, Dawson S G, Southerton G & Harris J W (1983) Non-volatile fatty acids in the diagnosis of non-specific vaginitis. *J Clin Pathol* 36(12): 1367-1370.
22. Piot P, Van Dyck E, Godts P & Vanderheyden J (1982) The vaginal microbial flora in non-specific vaginitis. *Eur J Clin Microbiol* 1(5): 301-306.
23. Al-Mushrif S, Eley A & Jones B M (2000) Inhibition of chemotaxis by organic acids from anaerobes may prevent a purulent response in bacterial vaginosis. *J Med Microbiol* 49(11): 1023-1030.
24. Kaneuchi C, Seki M & Komagata K (1988) Production of succinic acid from citric acid and related acids by *Lactobacillus* strains. *Appl Environ Microbiol* 54(12): 3053-3056.
25. Sohling B & Gottschalk G (1996) Molecular analysis of the anaerobic succinate degradation pathway in *Clostridium kluyveri*. *J Bacteriol* 178(3): 871-880.
26. Scherf U, Sohling B, Gottschalk G, Linder D & Buckel W (1994) Succinate-ethanol fermentation in *Clostridium kluyveri*: Purification and characterisation of 4-hydroxybutyryl-CoA dehydratase/vinylacetyl-CoA delta 3-delta 2-isomerase. *Arch Microbiol* 161(3): 239-245.
27. Macklaim J M, et al (2013) Comparative meta-RNA-seq of the vaginal microbiota and differential expression by *Lactobacillus iners* in health and dysbiosis. *Microbiome* 1(1): 12-2618-1-12.
28. Liebich H M & Forst C (1984) Hydroxycarboxylic and oxocarboxylic acids in urine: Products from branched-chain amino acid degradation and from ketogenesis. *J Chromatogr* 309(2): 225-242.
29. Kawai S, et al (1996) Purification and characterization of a malic enzyme from the ruminal bacterium *Streptococcus bovis* ATCC 15352 and cloning and sequencing of its gene. *Appl Environ Microbiol* 62(8): 2692-2700.
30. Pine L, Malcolm G B, Brooks J B & Daneshvar M I (1989) Physiological studies on the growth and utilization of sugars by *Listeria* species. *Can J Microbiol* 35(2): 245-254.
31. Novak L & Loubiere P (2000) The metabolic network of *Lactococcus lactis*: Distribution of (14)C-labeled substrates between catabolic and anabolic pathways. *J Bacteriol* 182(4): 1136-1143.
32. Yeoman C J, et al (2013) A multi-omic systems-based approach reveals metabolic markers of bacterial vaginosis and insight into the disease. *PLoS One* 8(2): e56111.
33. Kohlmeier K A, Vardar B & Christensen M H (2013) Gamma-hydroxybutyric acid induces actions via the GABAB receptor in arousal and motor control-related nuclei: Implications for therapeutic actions in behavioral state disorders. *Neuroscience* 248: 261-277.
34. Absalom N, et al (2012) alpha4betadelta GABA(A) receptors are high-affinity targets for gamma-hydroxybutyric acid (GHB). *Proc Natl Acad Sci USA* 109(33): 13404-13409.
35. Connelly W M, Errington A C & Crunelli V (2013) Gamma-hydroxybutyric acid (GHB) is not an agonist of extrasynaptic GABAA receptors. *PLoS One* 8(11): e79062.
36. Laghi L, et al (2014) Rifaximin modulates the vaginal microbiome and metabolome in women affected by bacterial vaginosis. *Antimicrob Agents Chemother* 58(6): 3411-3420.
37. Gajer P, et al (2012) Temporal dynamics of the human vaginal microbiota. *Sci Transl Med* 4(132): 132ra52.
38. Gloor G B, et al (2010) Microbiome profiling by Illumina sequencing of combinatorial sequence-tagged PCR products. *PLoS One* 5(10): e15406.
39. Aitchison J (1986) The statistical analysis of compositional data. London: Chapman & Hall.
40. Fernandes A D, et al (2014) Unifying the analysis of high-throughput sequencing datasets: Characterizing RNA-seq, 16S rRNA gene sequencing and selective growth experiments by compositional data analysis. *Microbiome* 2: 15-2618-2-15.
41. Stein S. (1999) An integrated method for spectrum extraction and compound identification from GC/MS data. *J Am Soc Mass Spectrom* 10: 70-781.
42. Styczynski M P, et al (2007) Systematic identification of conserved metabolites in GC/MS data for metabolomics and biomarker discovery. *Anal Chem* 79(3): 966-973.
43. Kessner D, Chambers M, Burke R, Agus D & Mallick P (2008) ProteoWizard: Open source software for rapid proteomics tools development *Bioinformatics* 24(21): 2534-2536.
44. Pluskal T, Castillo S, Villar-Briones A & Oresic M (2010) MZmine 2: Modular framework for processing, visualizing, and analyzing mass spectrometry-based molecular profile data *BMC Bioinformatics* 11: 395-2105-11-395.
45. Smith C A, et al (2005) METLIN: A metabolite mass spectral database. *Ther Drug Monit* 27(6): 747-751.
46. Wishart D S, et al (2013) HMDB 3.0—the human metabolome database in 2013. *Nucleic Acids Res* 41(Database issue): D801-7.
47. Lopez-Raton, M. et al. (2014) Optimal Cutpoints: An R Package for Selecting Optimal Cutpoints in Diagnostic Tests. *J Stat Softw.* 61: 1-36.
48. Youden W J (1950) Index for rating diagnostic tests. *Cancer* 3(1): 32-35.
49. Friedman, J. & Alm, E. J. Inferring correlation networks from genomic survey data. PLoS Comput. Biol. 8, e1002687 (2012).
50. Fernandes, A. D., Macklaim, J. M., Linn, T. G., Reid, G. & Gloor, G. B. ANOVA-like differential expression (ALDEx) analysis for mixed population RNA-Seq. PLoS One 8, e67019 (2013).
51. Benjamini, Y. & Hochberg, Y. Controlling the false discovery rate: A practical and powerful approach to multiple testing. J. R. Statist. Soc. B. 57, 289-300 (1995).

Through the embodiments that are illustrated and described, the currently contemplated best mode of making and using the invention is described. Without further elaboration, it is believed that one of ordinary skill in the art can, based on the description presented herein, utilize the present invention to the full extent. All publications cited herein are incorporated by reference.

Although the description above contains many specificities, these should not be construed as limiting the scope of the invention, but as merely providing illustrations of some of the presently embodiments of this invention.

What is claimed is:

1. A method of diagnosing bacterial vaginosis (BV) in a female mammal subject comprising:
   (a) obtaining a vaginal fluid sample from the subject;
   (b) detecting the presence of at least one of bacterial 2-hydroxyisovalerate (2HV) and bacterial γ-hydroxybutyrate (GHB) in the vaginal fluid sample, wherein the presence of at least one of bacterial 2HV and bacterial GHB indicates BV diagnosis in the female human subject, and
   (c) administering to the female mammal subject a drug effective to treat BV only when at least one of 2HV and GHB is present in the vaginal fluid sample.

2. The method of claim 1, wherein the method further comprises detecting the presence of another metabolite in the vaginal fluid sample, and a ratio of the at least one of bacterial 2HV and bacterial GHB to another metabolite in the sample is calculated, and wherein said diagnosis is based on the ratio.

3. The method of claim 1, wherein the presence of bacterial 2HV or bacterial GHB is detected using high performance liquid chromatography, thin layer chromatography (TLC), electrochemical analysis, Mass Spectroscopy (MS), refractive index spectroscopy (RI), Ultra-Violet spectroscopy (UV), fluorescent analysis, radiochemical analysis, Near-InfraRed spectroscopy (Near-IR), Nuclear Magnetic Resonance spectroscopy (NMR), fluorescence spectroscopy, dual polarisation interferometry, computational methods, Light Scattering analysis (LS), gas chromatography (GC), or GC coupled with MS (GC-MS), direct injection (DI) coupled with LC-MS/MS.

4. The method of claim 1, wherein the method further comprises detecting the present of tyrosine in the sample, and wherein the presence of the at least one of bacterial 2HV and bacterial GHB is detected using GC-MS, receiver operating characteristics curves are built from the GC-MS data, an area under the curve for bacterial 2HV, bacterial GHB and tyrosine in the sample are calculated, and a ratio of the area under the curve of at least one of bacterial 2HV and bacterial GHB to tyrosine in the sample is calculated, and wherein said diagnosis is based on the ratio.

5. The method of claim 4, wherein the ratio of bacterial GHB to tyrosine is 0.6 or above for BV diagnosis.

6. The method according to claim 1, wherein the method does not rely on the presence or level of succinate in the sample.

7. The method of claim 1, wherein the method further comprises specific pathogenic bacterial quantification.

8. The method of claim 7, wherein the specific pathogenic bacteria is selected from the group consisting of *G. vaginalis* and bacteria of the genera *Dialister, Prevotella* and *Atopobium*.

9. The method of claim 1, wherein prior to step (b) the method further comprises incubating the vaginal fluid sample under anaerobic condition and extracting metabolites from the incubated vaginal fluid sample, and wherein step (b) comprises detecting the presence of at the least one of bacterial 2-hydroxyisovalerate (2HV) and bacterial γ-hydroxybutyrate (GHB) among the extracted metabolites.

10. The method of claim 1, wherein the effective drug is an anti-*G. vaginalis* drug only when the bacterial GHB is present in the sample.

11. The method of claim 1, wherein the effective drug is a drug effective against bacteria of the genera *Dialister, Prevotella* and *Atopobium* only when the bacterial 2HV is present in the sample.

12. The method of claim 1, wherein only when both the bacterial 2HV and GHB are present in the sample, the effective drug is a combination of an anti-*G. vaginalis* drug and a drug effective against bacteria of the genera *Dialister, Prevotella* and *Atopobium*.

13. The method of claim 1, wherein the method further comprises obtaining the levels of the at least one 2HV and GHB in the vaginal fluid sample of step (a).

14. The method of claim 13, wherein when the female mammal subject is administered the drug effective to treat BV, the method further comprises obtaining a follow up vaginal fluid sample from the female mammal subject and obtaining the levels of the at least one of the 2HV and bacterial GHB the follow up vaginal fluid sample, wherein a decrease or increase in the levels of the at least one of 2HV and GHB in the follow up vaginal fluid sample relative to the vaginal fluid sample of step (a) is indicative of the efficacy of the treatment.

* * * * *